US011299552B2

(12) United States Patent
Yankee et al.

(10) Patent No.: US 11,299,552 B2
(45) Date of Patent: Apr. 12, 2022

(54) ELIMINATING MHC RESTRICTION FROM THE T CELL RECEPTOR AS A STRATEGY FOR IMMUNOTHERAPY

(71) Applicant: University of Kansas, Lawrence, KS (US)

(72) Inventors: Thomas Yankee, Overland Park, KS (US); John Szarejko, Liberty, MO (US)

(73) Assignee: University of Kansas, Lawrence, KS (US)

( * ) Notice: Subject to any disclaimer, the term of this patent is extended or adjusted under 35 U.S.C. 154(b) by 79 days.

(21) Appl. No.: 16/177,740

(22) Filed: Nov. 1, 2018

(65) Prior Publication Data

US 2019/0055318 A1     Feb. 21, 2019

Related U.S. Application Data

(63) Continuation of application No. PCT/US2017/030567, filed on May 2, 2017.

(60) Provisional application No. 62/330,499, filed on May 2, 2016.

(51) Int. Cl.

| C07K 16/30 | (2006.01) |
| A61K 39/39 | (2006.01) |
| C07K 14/705 | (2006.01) |
| C07K 16/28 | (2006.01) |
| C07K 14/725 | (2006.01) |
| C07K 16/00 | (2006.01) |
| A61K 38/17 | (2006.01) |
| C07K 14/495 | (2006.01) |
| C07K 14/65 | (2006.01) |
| C12N 15/113 | (2010.01) |
| C12N 15/62 | (2006.01) |
| A61K 38/10 | (2006.01) |

(52) U.S. Cl.
CPC ........ *C07K 16/3092* (2013.01); *A61K 38/179* (2013.01); *A61K 39/39* (2013.01); *C07K 14/495* (2013.01); *C07K 14/65* (2013.01); *C07K 14/7051* (2013.01); *C07K 14/70532* (2013.01); *C07K 14/70578* (2013.01); *C07K 14/70596* (2013.01); *C07K 16/00* (2013.01); *C07K 16/2803* (2013.01); *C07K 16/2896* (2013.01); *C07K 16/3084* (2013.01); *C12N 15/113* (2013.01); *C12N 15/62* (2013.01); *A61K 38/10* (2013.01); *C07K 2317/622* (2013.01); *C07K 2319/03* (2013.01); *C07K 2319/33* (2013.01); *C07K 2319/42* (2013.01)

(58) Field of Classification Search
CPC ............ C07K 2317/62; C07K 2319/30; C07K 2319/33
USPC ..................................................... 424/133.1
See application file for complete search history.

(56) References Cited

U.S. PATENT DOCUMENTS

| 8,399,645 | B2 | 3/2013 | Campana et al. |
| 8,815,247 | B2 | 8/2014 | Govindappa et al. |
| 8,906,682 | B2 | 12/2014 | June et al. |
| 9,233,125 | B2 | 1/2016 | Davila et al. |
| 9,447,194 | B2 | 9/2016 | Jensen |
| 2002/0102233 | A1 | 8/2002 | Ashkenazi |
| 2005/0113564 | A1 | 5/2005 | Campana et al. |
| 2006/0235201 | A1 | 10/2006 | Kischel |
| 2012/0114700 | A1 | 5/2012 | Samelson et al. |
| 2012/0122182 | A1 | 5/2012 | Tannous et al. |
| 2012/0190828 | A1 | 7/2012 | Jakobsen et al. |
| 2013/0071414 | A1 | 3/2013 | Dotti et al. |
| 2013/0280220 | A1 | 10/2013 | Ahmed et al. |
| 2014/0134142 | A1 | 5/2014 | Smith et al. |
| 2014/0271582 | A1 | 9/2014 | Forman et al. |
| 2014/0349402 | A1 | 11/2014 | Cooper et al. |
| 2015/0024482 | A1 | 1/2015 | Frigault et al. |
| 2015/0238631 | A1 | 8/2015 | Kim et al. |
| 2015/0274827 | A1 | 10/2015 | Pfizenmaier et al. |
| 2016/0096902 | A1 | 4/2016 | Cooper et al. |
| 2016/0207989 | A1 | 7/2016 | Short |
| 2016/0340649 | A1 | 11/2016 | Brown et al. |
| 2019/0309307 | A1* | 10/2019 | Garcia ............... C12N 15/1138 |

(Continued)

FOREIGN PATENT DOCUMENTS

| JP | 2011019467 A | 2/2011 |
| WO | WO-2015/166056 A1 | 11/2015 |
| WO | WO-2015/188141 A9 | 12/2015 |

(Continued)

OTHER PUBLICATIONS

Long et al. (Cancer Immunol Res; 4(10); 869-880 (2016)).*
Park et al. (Molecular Therapy vol. 15 No. 4, 825-833 (Apr. 2007)).*
Pule et al. (Nat Med. 14(11): 1264-1270 (Nov. 2008)).*
Szarejko et al. (Molecular Therapy 24 Suppl. 1, pp. S256 (Apr. 2016)).*

(Continued)

*Primary Examiner* — Lynn A Bristol
(74) *Attorney, Agent, or Firm* — Foley & Lardner LLP

(57) ABSTRACT

The present disclosure generally relates to chimeric antigen receptors, more specifically to chimeric antigen receptor compositions and methods for use of the same. The present disclosure also provides for nucleic acid molecules and expression vectors for making and using the chimeric antigen receptors and for co-receptor signaling using such chimeric antigen receptors. The present disclosure also provides methods of treatment using such compositions. The chimeric antigen receptors of the present disclosure interact with the endogenous T-cell receptor complex enabling physiological control of signaling and T-cell response and can be combined with ligands such as co-stimulatory ligands for further controlling and influencing T-cell activation and response.

8 Claims, 14 Drawing Sheets

Specification includes a Sequence Listing.

(56) References Cited

U.S. PATENT DOCUMENTS

2021/0000873 A1* 1/2021 Dekosky ............... A61P 35/00

FOREIGN PATENT DOCUMENTS

| WO | WO-2016/016343 | A1 | 2/2016 |
|---|---|---|---|
| WO | WO-2016/055551 | A1 | 4/2016 |
| WO | WO-2016/069283 | A1 | 5/2016 |
| WO | WO-2016/187349 | A1 | 11/2016 |
| WO | WO-2016/210447 | A1 | 12/2016 |

OTHER PUBLICATIONS

Thanindratarn et al. (Cancer Treatment Reviews 82:101934 (2020)).*
Walseng et al. (Nature 7:10713 (Sep. 2017)).*
GenBank Accession No. DQ904462, Sep. 26, 2006 [online]. [Retrieved on Sep. 6, 2017]. Retrieved from internet: <URL: https://www.ncbi.nlm.nih.gov/nuccore/DQ904462> Entire Document.
GenBank Accession No. AB590869, Sep. 25, 2010 [online]. [Retrieved on Sep. 6, 2017]. Retrieved from internet: <URL: https://www.ncbi.nlm.nih.gov/nuccore/307686186?sat=3&satkey=15299530> Entire Document.
GenBank Accession No. AY891204, Mar. 21, 2005 [online]. [Retrieved on Sep. 6, 2017]. Retrieved from internet: <URL: https://www.ncbi.nlm.nih.gov/nuccore/61368215?sat=4&satkey=9084986> Entire Document.
Morgan et al., Cancer Regression in Patients After Transfer of Genetically Engineered Lymphocytes, Science. Oct. 6, 2006, vol. 314, No. 5796, pp. 126-129 (author manuscript pp. 1-10). Especially p. 1, para 2.
Bridgeman, J.S., et al., "CD3zeta-based chimeric antigen receptors mediate T cell activation via cis- and trans-signaling mechanisms: implications for optimization of receptor structure for adoptive cell therapy," Clinical and Experimental Immunology, 175:258-267 (2013) (10 pages).
Bridgeman, J.S., et al., "The Optimal Antigen Response of Chimeric Antigen Receptors Harboring the CD3zeta Transmembrane Domain is Dependent upon Incorporation of the Receptor into the Endogenous TCR/CD3 Complex," J. Immunol., 184:6938-6949 (2010) (20 pages).
Wyzgol, A., et al., "Trimer Stabilization, Oligomerization, and Antibody-Mediated Cell Surface Immobilization Improve the Activity of Soluble Trimers of CD27L, CD40L, 41BBL, and Glucocorticoid-Induced TNF Receptor Ligand," J. Immunol., 183:1851-1861 (2009) (12 pages).
International Search Report and Written Opinion on PCT/US2017/030567 dated Sep. 25, 2017 (17 pages).

* cited by examiner

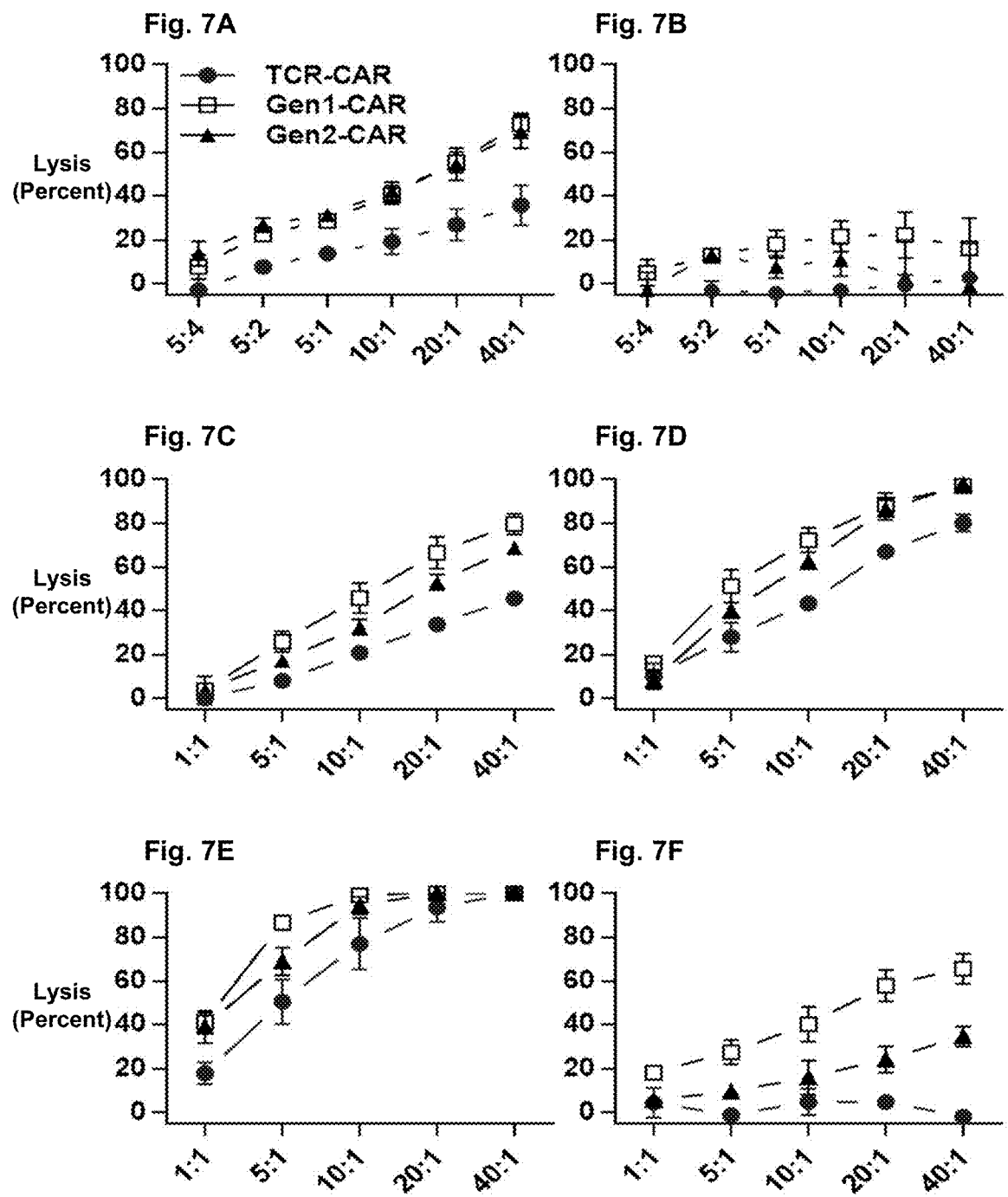

Figure 9B
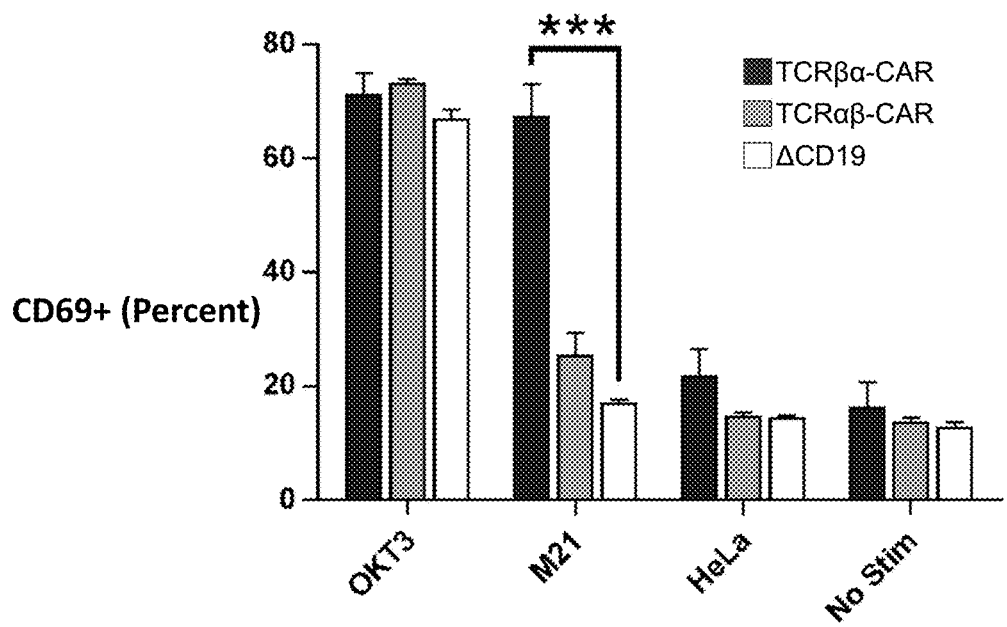
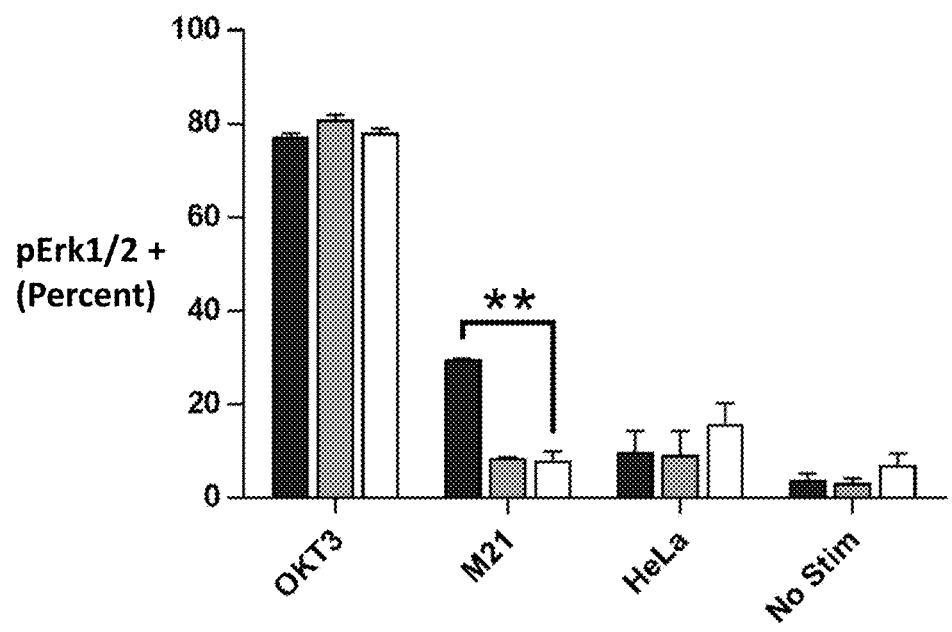

ELIMINATING MHC RESTRICTION FROM THE T CELL RECEPTOR AS A STRATEGY FOR IMMUNOTHERAPY

CROSS-REFERENCE TO RELATED APPLICATIONS

The present application is a continuation of International Application No. PCT/US17/30567, filed May 2, 2017, and claims priority to U.S. Provisional Application No. 62/330,499, filed on May 2, 2016 which is herein incorporated by reference in its entirety.

SEQUENCE LISTING

The instant application contains a Sequence Listing which has been filed electronically in ASCII format and is hereby incorporated by reference in its entirety. Said ASCII copy, created on May 2, 2017, is named 17-21007-WO_SL.txt and is 66,321 bytes in size.

FIELD OF THE INVENTION

The present disclosure generally relates to chimeric antigen receptors, more specifically to chimeric antigen receptor compositions and methods for use of the same. The present disclosure also provides for nucleic acid molecules and expression vectors for making and using the chimeric antigen receptors and for co-receptor signaling using such chimeric antigen receptors. The present disclosure also provides methods of treatment using such compositions.

BACKGROUND OF THE INVENTION

Chimeric antigen receptors (CARs) are used to redirect patients' T cells towards tumor cells to destroy malignant cells. Despite impressive response rates for B cell malignancies, clinical outcomes have been disappointing for the treatment of most cancers and CAR therapy is highly toxic, commonly inducing cytokine release syndrome and on-target/off-tumor effects. Some clinical limitations of CARs may be attributed to the unregulated surface expression and functionality of CARs, which lack key regulatory components inherent to the endogenous T cell receptor (TCR) complex.

Previously developed CAR designs are generally monomeric proteins consisting of a single chain antibody fragment (scFv) fused to linker, transmembrane and signaling domains of receptors capable of activating T cells. The signaling component in first generation CARs (gen1-CAR) was commonly TCR $\zeta$ chain while second generation CARs added the signaling domain from a co-receptor, such as 4-1BB. Third generation CARs combined multiple co-receptors into a single construct. However, these constructs do not permit regulation of downstream signaling pathways. By contrast, the endogenous T cell receptor (TCR) is a large multimeric complex whose expression and function is tightly regulated, which restricts the kinetics and intensity of signaling. This regulation enables TCR signaling to drive distinct biological outcomes depending on antigen expression and affinity.

The TCR complex consists of at least eight proteins and ten immunoreceptor tyrosine-based activation motifs (ITAMs), which is in direct contrast to monomeric $\zeta$ chain-containing CARs that only contain three ITAMs. Multiple signaling proteins bind endogenous CD3 chains, a feature that cannot be replicated using monomeric CARs. Although some $\zeta$ chain-based CARs can associate with the TCR and activate ZAP-70, MAPK, and NF-AT, the signalizing pathways are dysregulated and CAR-expressing cells are highly active.

In view of the foregoing, an unmet need exists for a novel platform for CAR therapy that is less toxic and more broadly applicable than other CARs and which can utilize the endogenous regulation of the TCR complex to improve sensitivity, limit toxicity, incidence of cytokine release syndrome and off-tumor effects.

SUMMARY

The present disclosure generally relates to chimeric antigen receptors, more specifically to chimeric antigen receptor compositions and methods for use of the same. The present disclosure also provides for nucleic acid molecules and expression vectors for making and using the chimeric antigen receptors and for co-receptor signaling using ligands fused to antigen-specific peptides. The present disclosure also provides methods of treatment using such compositions.

In an embodiment, a construct includes a 4-1BB ligand (4-1BBL) fused to a peptide that is capable of specifically binding a tumor-specific antigen.

In some embodiments, a nucleic acid molecule encodes the construct including 4-1BBL fused to a peptide that is capable of specifically binding a tumor-specific antigen.

In some embodiments, a modified T lymphocyte expresses a construct including 4-1BBL fused to a peptide that is capable of specifically binding a tumor-specific antigen and a chimeric antigen receptor. In some embodiments, the chimeric antigen receptor includes a T-cell receptor beta chain constant region and a T-cell receptor alpha chain constant region wherein the T-cell receptor beta chain constant region is fused to a peptide having an affinity to an antigen, and wherein the T-cell receptor beta chain constant region is complexed with the T-cell receptor alpha chain constant region. In some embodiments, the chimeric antigen receptor does not include a T-cell receptor beta chain variable region and a T-cell alpha chain variable region. In some embodiments, a modified T lymphocyte expresses a construct including a chimeric antigen receptor includes a T-cell receptor beta chain constant region and a T-cell receptor alpha chain constant region wherein the T-cell receptor beta chain constant region is fused to a peptide having an affinity to an antigen, and wherein the T-cell receptor beta chain constant region is complexed with the T-cell receptor alpha chain constant region.

In some embodiments, a recombinant expression vector is provided which includes a nucleic acid molecule encoding the ligand fused to a peptide that is capable of specifically binding a tumor-specific antigen and/or a chimeric antigen receptor including a T-cell receptor beta chain constant region and a T-cell receptor alpha chain constant region wherein the T-cell receptor beta chain constant region is fused to a peptide having an affinity to an antigen, and wherein the T-cell receptor beta chain constant region is complexed with the T-cell receptor alpha chain constant region. In some embodiments, the chimeric antigen receptor does not include a T-cell receptor beta chain variable region and a T-cell alpha chain variable region.

In some embodiments, a method is provided for treating cancer in a subject a modified T-lymphocyte of the present disclosure.

DESCRIPTION OF THE DRAWINGS AND FIGURES

The foregoing aspects and many of the attendant advantages of this invention will become more readily appreciated as the same become better understood by reference to the following detailed description, when taken in conjunction with the accompanying drawings.

FIG. 1A is a schematic representation of the cDNA constructs.

FIG. 1B shows a T-cell receptor-based chimeric antigen receptor of the present disclosure complexed with the endogenous T-cell receptor subunits, a gen1-CAR and a gen2-CAR with a 4-1BB signaling domain. Numerical designations (1)-(8) reference the following: (1) scFv; (2) conserved antigen receptor transmembrane motif; (3) basic rich stretch; (4) proline-rich sequence; (5) immunoreceptor tyrosine-based activation motif (ITAM); (6) CD28 hinge/transmembrane domain; (7) CD3ζ signaling domain; and (8) 41BB signaling domain.

FIG. 7A shows a graph illustrating the effect of transducing Primary T cells with each construct and incubated with M21 and after four hours, the number of remaining cells were calculated and normalized according to cytolysis by ΔCD19 cells (n=5).

FIG. 7B shows a graph illustrating the effect of transducing Primary T cells with each construct and incubated with HeLa and after four hours, the number of remaining cells were calculated and normalized according to cytolysis by ΔCD19 cells (n=5).

FIG. 7C shows a graph illustrating the effect of incubating purified, transduced CD8$^+$ T cells with M21 cells for 4 hours, with specific lysis calculated (n=3).

FIG. 7D shows a graph illustrating the effect of incubating purified, transduced CD8$^+$ T cells with M21 cells for 8 hours, with specific lysis calculated (n=3).

FIG. 7E shows a graph illustrating the effect of incubating purified, transduced CD8$^+$ T cells with M21 cells for 24 hours, with specific lysis calculated (n=3).

FIG. 7F shows a graph illustrating the effect of incubating purified, transduced CD8$^+$ T cells with HeLa cells for 4 hours, with specific lysis calculated (n=3).

FIG. 9B shows graphs depicting data and a summary (mean±S.E.M.) of replicates for phosphor-ERK expression ($***p<0.0001$, n=2-3).

DETAILED DESCRIPTION OF THE INVENTION

Figure 1A:
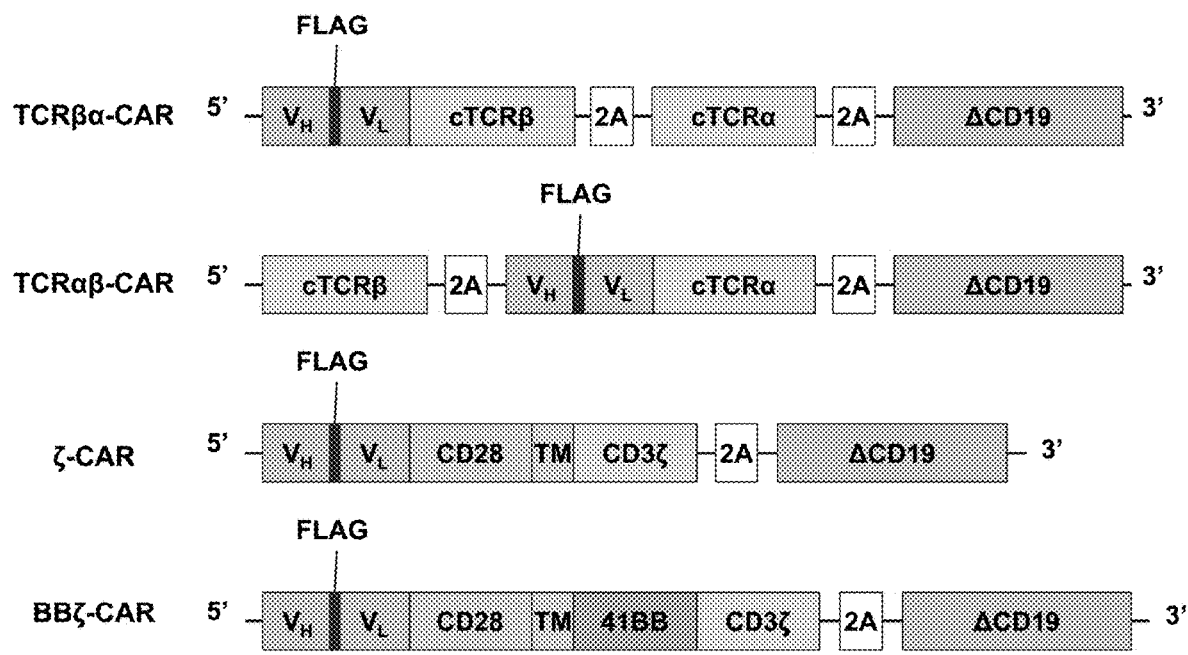

The present disclosure describes particular embodiments and with reference to certain drawings, but the subject matter is not limited thereto. The drawings described are only schematic and are non-limiting. In the drawings, the size of some of the elements may be exaggerated or distorted and not drawn to scale for illustrative purposes. Where the elements of the disclosure are designated as "a" or "an" in first appearance and designated as "the" or "said" for second or subject appearances unless something else is specifically stated.

The present disclosure will provide description to the accompanying drawings, in which some, but not all embodiments of the subject matter of the disclosure are shown. Indeed, the subject matter may be embodied in many different forms and should not be construed as limited to the embodiments set forth herein, rather, these embodiments are provided so that this disclosure satisfies all the legal requirements.

Certain terminology is used in the following description for convenience only and is not limiting. Certain words used herein designate directions in the drawings to which reference is made. Unless specifically set forth herein, the terms "a," "an" and "the" are not limited to one element, but instead should be read as meaning "at least one." As used herein "another" means at least a second or more. The terminology includes the words noted above, derivatives thereof and words of similar import.

The use of the term "or" in the claims is used to mean "and/or" unless explicitly indicated to refer to alternatives only or the alternatives are mutually exclusive.

Use of the term "about", when used with a numerical value, is intended to include+/−10%. For example, if a number of amino acids is identified as about 200, this would include 180 to 220 (plus or minus 10%).

Unless otherwise defined, all technical and scientific terms used herein have the same meaning as commonly understood by one of ordinary skill in the art.

All patents and publications cited herein are incorporated by reference in their entirety, including any references cited therein.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, one skilled in the art will understand that an antigen need not be encoded solely by a full length nucleotide sequence of a gene.

"Single chain variable fragment" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding.

The term "promoter" as used herein is defined as a DNA sequence recognized by the transcriptional machinery of the cell, or introduced transcriptional machinery, required to initiate the specific transcription of a polynucleotide sequence.

The present disclosure generally relates to chimeric antigen receptors, more specifically to chimeric antigen receptor compositions and methods for use of the same. The present disclosure also provides for nucleic acid molecules and expression vectors for making and using the chimeric antigen receptors and for co-receptor signaling using such chimeric antigen receptors. The present disclosure also provides methods of treatment using such compositions.

The present disclosure is based on the discovery that a T-cell receptor-based chimeric antigen receptor (TCAR) can exhibit improved properties over currently developed CARs. Specifically, such TCARs can reduce T-cell exhaustion, cytokine release syndrome (CRS), which is caused by the release of vast quantities of cytokines and may result in high fever, tachycardia, cardiac dysfunction, and end-organ failure, and off-tumor effects which are challenges with conventional chimeric antigen receptors. The incidence of CRS correlates with disease burden at the time of CAR infusion but does not correlate with clinical outcome.

The clinical limitations of previously developed CARs may be caused by several factors. First, such CARs are constitutively active and lack key regulatory components inherent to the endogenous T cell receptor complex. This unregulated surface expression and functionality can result in T-cell exhaustion and overstimulation of the T-cell response. This can result in increased cytokine production which can cause CRS. Further, because antigens are often expressed at high levels on tumor cells and low levels on healthy cells, previously developed chimeric antigen receptors cannot distinguish between cells with varying levels of antigen.

By combining the antigen recognition capacity of CARs with the functionality of the T-cell receptor complex these drawbacks of previously developed CARs can be avoided and/or reduced. The T-cell receptor-based CARs of the present disclosure demonstrate surface expression that is limited by the endogenous CD3 proteins which results in more regulated surface expression. Further, such TCARs demonstrate a higher threshold of activation which suggests that off-tumor effects can be limited and also induce cytokine production at a more physiological level than previously developed CARs, which can reduce the incidence of CRS. In addition, the TCARs of the present disclosure can selectively lyse antigen-expressing tumor cells while sparing antigen-negative tumor cells. Thus, the TCARs of the present disclosure can be less toxic than previously developed CARs. By allowing physiological regulatory mechanisms to control the kinetics and duration of downstream signals, optimal transcription of immunologically critical genes, such as IL-2 and IL-8, can be assured.

Further, in some aspects, the use of co-receptor ligands with the T CARs of the present disclosure can allow for inducible activation of co-receptor signals which can enable tighter control of the receptors to allow for physiological regulatory mechanisms to control the kinetics and intensity of downstream signals to ensure optimal transcription of immunological critical genes. This can provide more efficient tumor destruction than constitutively active signaling and can reduce T-cell exhaustion, cytokine release syndrome (CRS) and off-tumor effects. The present disclosure combines the antigen recognition capacity of CARs with the functionality of the TCR complex. By way of example but not limitation, a modified T cell expressing a TCAR of the present disclosure can be activated upon binding to a target antigen which can stimulate expression of the 4-1BB receptor. When a secreted co-receptor ligand fused to a peptide for a tumor-specific antigen on the surface of the same cell is expressed by the modified T cell, for example the 4-1BB ligand, it can then bind to the now expressed 4-1BB receptor and result in an inducible response that is physiological rather than a constitutively active response as observed with gen2-CAR with an intracellular 4-1BB signaling domain. In certain instances, the ligand could be attached to the T-cell receptor-based CAR of the present disclosure as this would still permit an inducible response.

FIG. 1A shows exemplary CARs of the present disclosure (TCRβα-CAR and TCRαβ-CAR), a gen1-CAR (ζ-CAR) and a gen2-CAR (Bζ-CAR). All of the constructs include a scFv with embedded FLAG tag ($V_H$-FLAG-$V_L$), 2A linker sequences and a ΔCD19 tail as discussed further in the Examples. The exemplary CARs of the present disclosure also include a T-cell receptor alpha chain constant region (cTCRα) and a T-cell receptor beta constant region (cTCRβ) and an additional, in some instances different 2A linker. The gen1-CAR and gen2-CAR shown include a CD28 hinge region, a transmembrane domain, and the CD3ζ chain. gen2-CAR also includes a 41BB signaling domain.

Figure 1B:
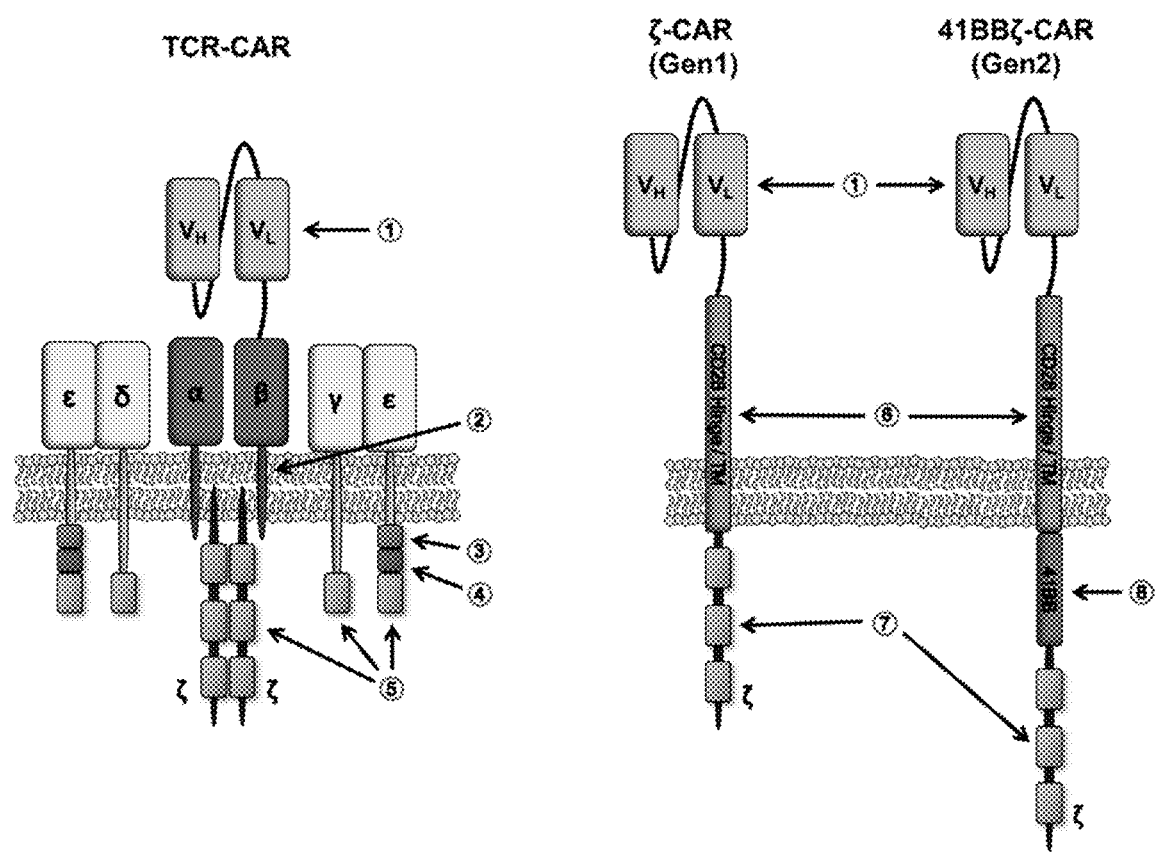

The T-cell receptor-based CARs of the present disclosure are able to associate with other endogenous subunits of the TCR as shown in FIG. 1B. FIG. 1B shows the assembly of TCRαβ-CAR or TCRβα-CAR (TCR-CAR) with the endogenous TCR complex as well as the gen1-CAR and gen2-CAR in the cellular membrane. Each CAR includes a scFv sequence (1). The scFv in the TCR-CAR is linked to the T-cell receptor beta constant region which is complexed with the T-cell receptor alpha constant region and includes a conserved antigen receptor transmembrane motif (2) which is located in the TCRβ transmembrane domain and involved in TCR polarization and NF-κB recruitment to the immunological synapse and required for the formation of memory cells. The CD3ε subunit includes a basic rich stretch (3) which modulates TCR signaling and recruitment to the immunological synapse through ITAM accessibility and a proline rich sequence (4) which is involved in actin cytoskeleton reorganization and formation of the immunological synapse. ITAMs (5) of the CDγ, CDε, CDδ and CDζ subunits can be phosphorylated which recruits Zap-70 which activates signaling pathways important for T cell survival, proliferation, differentiation, and effector functions. The degree of ITAM accessibility modulates TCR signaling.

In contrast, the gen1-CAR (ζ-CAR) shown in FIG. 1B includes a scFv sequence (1), a CD28 hinge/transmembrane domain (6) which acts as a scaffold for scFv surface expression and attachment of intracellular signaling domains and a CD3ζ signaling domain (7) which allows for signaling through TCR pathways. The gen2-CAR (41Bζ-CAR) includes these features as well as an intracellular 41BB signaling domain (8) which provides signals necessary for sustained survival and effector functions. As can be observed, the T-cell receptor-based CARs of the present disclosure allow the constructs to associate with other components of the TCR complex which can limit the surface expression of the TCAR by the availability of CD3 proteins. By comparison, the surface expression of gen1-CAR and gen2-CAR are only limited by gene copy number and promoter strength.

By restricting the surface expression of the scFv-TCRβ/TCRα complex, it is believed without being bound by theory that this limits the tonic signaling associated with the high surface expression of gen1-CAR and gen2-CARs.

In some embodiments a construct includes a ligand fused to a peptide that is capable of specifically binding a tumor-specific antigen. In some aspects, the ligand can be a co-stimulator ligand that binds a cognate co-stimulatory molecule, e.g. a receptor, on a T cell that stimulates the T cell to effect a response.

In some embodiments, the ligand is the 4-1BB ligand (4-1BBL). In some embodiments, the amino acid sequence of the ligand may be modified, e.g. by deletion, insertion, addition, substitution, or truncation, as compared to its native amino acid sequence. For example, the 4-1BBL used may have an amino acid sequence of SEQ ID NO: 1, amino acids 85-254 of the full-length, native 4-1BBL amino acid sequence, where there is a mutation of E254D and addition of H255 to the native amino acid sequence of 4-1BBL, which is encoded by SEQ ID NO: 2. In some embodiments, the ligand is void of its transmembrane domain. For example, the 4-1BBL of SEQ ID NO: 1 does not contain the transmembrane domain, amino acids 29-49, of the full-length, native amino acid sequence of 4-1BBL. In some embodiments, the ligand has a mutation in its trimerization domain. For example, for 4-1BBL or a variant thereof such as that of SEQ ID NO: 1, the amino acids corresponding to positions 94, 142, 144, 199, 204, 234 and/or 238 of the full-length, native amino acid sequence may be mutated. The ligand may be selected based on the co-receptor target. By way of example but not limitation, in certain alternative embodiments the ligand can be 4-1BBL, CD80, CD58, OX40L, MICA, ICAM-1, CD5 ligand or CD48 which bind to the 4-1BB, CD28, CD2, OX40, NKG2D, LFA-1, CD5 and 2B4 receptors, respectively. In some embodiments, the intracellular domain can be fused to the C-terminus of the scFv-TCRβ via a lengthy, flexible linker domain that will extend the ligand further than the membrane than through the endogenous CD3 and ζ chains.

The peptide can be any amino acid sequence that can specifically bind to an antigen, in some aspects, a tumor-specific antigen. In some embodiments, the peptide is a single chain variable fragment (scFv). In some embodiments the peptide is an antibody or other protein with an affinity for binding an antigen. The tumor-specific antigen can be any antigen which is specifically expressed by or more highly expressed by tumor cells as compared to non-tumor cells. By way of example but not limitation, the tumor-specific antigen can be selected from the group consisting of disialoganglioside GD2 (GD2), mucin 1 (MUC1), prostate-specific membrane antigen (PSMA), human epidermal growth factor receptor 2 (Her2), mucin 16 (MUC16), melanoma-associated antigen 1(MAGE-A1), carbonic anhydrase 9 (CAIX), b-lymphocyte surface antigen CD19 (CD19), prominin-1 (CD133), CD33 antigen (CD33), CD38 antigen (CD38), neural cell adhesion molecule (CD56), interleukin-3 receptor (CD123), and b-lymphocyte antigen CD20 (CD20). By way of example but not limitation, the peptide can be anti-GD2 scFv of SEQ ID NO: 16 encoded by SEQ ID NO: 17.

In some embodiments a chimeric antigen receptor is provided which includes a T-cell receptor beta chain constant region and a T-cell alpha chain constant region, wherein the T-cell receptor beta chain constant region is fused to a peptide having affinity to an antigen, wherein the chimeric antigen receptor does not include a T-cell receptor beta chain variable region and a T-cell alpha chain variable region, and wherein the T-cell receptor beta chain constant region is complexed with the T-cell receptor alpha chain constant region. In some embodiments, the peptide having affinity to an antigen is a peptide as described in the foregoing embodiments and the antigen is any antigen including those described in the foregoing embodiments, in some aspects, a tumor-specific antigen. In some embodiments the peptide is a scFv as described in the foregoing embodiments. The peptide fused to the T-cell beta constant region can be the same or different from the peptide fused to the ligand in the foregoing embodiments.

In some embodiments, a nucleic acid molecule encodes a construct of any of the foregoing embodiments. In some embodiments, the nucleic acid molecule encodes a chimeric antigen receptor of any of the foregoing embodiments. In some embodiments, the nucleic acid molecule further includes a promoter region. The promoter region can be responsive to signaling through a T cell receptor. By way of example but not limitation, the promoter region can be derived from the human NF-AT promoter or from the Elk-1 pathway. For example, the promoter region can have the sequence of SEQ ID NO: 7, which includes a NF-AT response element encoded by SEQ ID NO: 8 and a mini promoter encoded by SEQ ID NO: 9. By way of example but not limitation, the nucleic acid molecule could have the sequence of SEQ ID NO: 10 encoding SEQ ID NO: 11, which encodes restriction sites, a NF-AT response element, mini promoter, anti-GD2 scFv, a linker (SEQ ID NO: 14) encoded by SEQ ID NO: 15, HA tag (SEQ ID NO: 12) encoded by SEQ ID NO:13, and 4-1BBL. By way of example but not limitation, the nucleic acid molecule could have the sequence of SEQ ID NO: 41 which encodes anti-GD2 scFv-T-cell receptor β constant region-P2A linker-T-cell receptor alpha constant region-T2A linker-ΔCD19-NF-AT Response Element-mini promoter-anti-GD2 scFv-HA tag-41BBL. By way of further example but not limitation, the nucleic acid molecule can include SEQ ID NO: 27 which encodes T-cell receptor β constant region-P2A linker-T-cell receptor alpha leader sequence-T-cell receptor alpha constant region which includes the T-cell receptor alpha leader sequence which can be used to ensure that the construct is transported to the cell membrane. Other leader sequences known to those of skill in the art can be used to direct the construct to the cell membrane. It should be understood that all of the constructs and nucleic acid molecules within the scope of the present disclosure can be modified to include a leader sequence.

In some embodiments, a modified T lymphocyte is provided which expresses a construct including a ligand fused to a peptide that is capable of specifically binding a tumor-specific antigen and a chimeric antigen receptor. In some embodiments, a modified T lymphocyte is provided which expresses a construct including a chimeric antigen receptor of any of the foregoing embodiments. In some embodiments, the chimeric antigen receptor includes a T-cell receptor beta chain constant region and a T-cell receptor alpha chain constant region, where the beta chain constant region is fused to a peptide having affinity to an antigen, and wherein the T-cell receptor beta chain constant region is complexed with the T-cell receptor alpha chain constant region. In some embodiments, the peptide having affinity to an antigen is a peptide as described in the foregoing embodiments and the antigen is any antigen including those described in the foregoing embodiments, in some aspects, a tumor-specific antigen. In some embodiments the peptide is a scFv as described in the foregoing embodiments. In some embodiments, the modified T lymphocyte expresses a chimeric antigen receptor of any of the foregoing embodiments. The peptide fused to the T-cell beta constant region can be the same or different from the peptide fused to the ligand in the foregoing embodiments. In some aspects, the construct including a ligand fused to a peptide that is capable of specifically binding a tumor-specific antigen can be fused to the chimeric antigen receptor, for example, by a 2A linker.

In some embodiments, a method is provided for treating cancer in a subject which includes the step of administering to the subject a modified T lymphocyte of any of the foregoing embodiments.

In some embodiments a recombinant expression vector comprises a nucleic acid molecule of any of the foregoing embodiments.

In any of the foregoing embodiments, the T-cell receptor alpha chain constant region can be the full-length, native T-cell receptor alpha chain constant region or any modified portion thereof. By way of example but not limitation, the T-cell receptor alpha chain constant region can have the sequence of SEQ ID NO: 5 encoded by SEQ ID NO: 6 which has a mutation of T42C to promote pairing with the T-cell receptor beta chain constant region. This modified sequence, when used in conjunction with a similar modification (S57C) to the T-cell receptor beta constant region helps to avoid mispairing between endogenous and exogenous T-cell receptor proteins by introducing a second disulfide bond between the exogenous T-cell receptor alpha constant region and T-cell receptor beta constant region.

In any of the foregoing embodiments, the T-cell receptor beta chain constant region can be the full-length, native T-cell receptor beta chain constant region or any modified portion thereof. By way of example but not limitation, the T-cell receptor beta chain constant region can have the sequence of SEQ ID NO: 3 encoded by SEQ ID NO: 4 which has a mutation of S57C to promote pairing with the T-cell receptor alpha chain constant region. This modified sequence, when used in conjunction with a similar modification (T42C) to the T-cell receptor beta constant region helps to avoid mispairing between endogenous and exogenous T-cell receptor proteins by introducing a second disulfide bond between the exogenous T-cell receptor alpha constant region and T-cell receptor beta constant region.

Linkers may be included in the TCARs of the present disclosure. By way of example but not limitation, such linkers can include SEQ ID NO: 18 and SEQ ID NO: 20, encoded by SEQ ID NO: 19 and SEQ ID NO: 21, respectively.

In some embodiments, alternative mechanisms by which 4-1BB can be activated can be used. For example, the intracellular domain of 4-1BB can be fused to the C-terminus of the constant region of TCRα, TCRβ, or other chains of the TCR complex (such as CD3δ) via a PRK linker. For example, SEQ ID NOs: 37, 35 and 33 which encode SEQ ID NOs: 36, 34 and 32, respectively, can be used to express TCRβα-PRK-41BB, TCRβ-PRK-41BB and CD3δ-PRK-41BB, respectively. In preliminary experiments, it has been found that direct fusion of the intracellular portion of 4-1BB to TCRα or TCRβ (i.e. without a linker), the TCAR is not expressed on the cell surface. Further preliminary data suggests that TCRβα-PRK-41BB and TCRβ-PRK-41BB possess enhanced function over CD3δ-PRK-41BB (as measured by increased expression of Bcl-xL).

Alternatively, two 4-1BB intracellular motifs can be expressed as a single protein in which the N-terminus has a membrane-localization sequence, trimerization motif, and a calmodulin switch motif is inserted in between the two 4-1BB domains. In this way, CAR-induced calcium mobilization would induce dimerization of 4-1BB on individual proteins and heximerization of the trimeric protein complex. For example, SEQ ID NO: 39 which encodes 41-BB-Calmodulin Switch (SigSeq-HA tag-TM-Trimerization Domain-41BB-NCaM-CKKp-CCaM-41BB could be used.

EXAMPLES

The present invention is demonstrated in the following examples, it being understood that these are for illustrative purposes only, and the invention is not intended to be limited thereto.

Materials and Methods

For all examples herein, the following materials and methods were used:

Plasmid Construction

Transgenes encoding CAR constructs were cloned into the pSFG retroviral transfer plasmid. The pSFG-T2A-ΔCD19 control plasmid containing cDNA encoding a 2A viral linker (SEQ ID NO: 21 encoding by SEQ ID NO: 20) and a ΔCD19 gene (SEQ ID NO: 23 encoded by SEQ ID NO: 22) was generated by Gibson Assembly® of a T2A-ΔCD19 gene fragment (Life Technologies) between the NcoI and XhoI restriction sites of pSFG. The gene fragment included a 5' multiple cloning site (NcoI, SphI, NsiI, AfeI, XhoI, SalI, SacII, BamHI) for cloning upstream of T2A and a 3' multiple cloning site (BsaBI, MluI, BsiWI, SnaBI, BstZ17I, MfeI, AleI) for cloning downstream of ΔCD19. A gene fragment encoding the anti-GD2 scFv (SEQ ID NO: 17) was cloned between the NcoI and SalI sites in pSFG-T2A-ΔCD19 and the subsequent plasmid used for generation of CAR constructs. For TCRβα-CAR (SEQ ID NO: 24, GD2 scFv-TCRβc-P2A-TCRαc-T2A-ΔCD19), gene fragments encoding human TCRβ (SEQ ID NO: 4) and P2A-TCRα (P2A of SEQ ID NO: 19 and TCRα of SEQ ID NO: 6) were cloned into the BamHI site. TCRβα-CAR19 was constructed by replacing the anti-GD2 scFv with anti-CD19 scFv (SEQ ID NO: 30 encoded by SEQ ID NO: 31) following NcoI/SalI restriction digest. The ΔCD19 transduction marker was subsequently replaced with ΔCD34 (SEQ ID NO: 28 encoded by SEQ ID NO: 29) using RsrII/MfeI digest. Gen1-CAR and gen2-CAR were generated by cloning gene fragments between SalI and BamHI sites.

Cell Lines and Antibodies

The M21 and A375 melanoma cell lines, HeLa adenocarcinoma cells, and HEK 293T cells were maintained in DMEM 10-013-CV (Corning Life Sciences, Corning, N.Y.) supplemented with 10% fetal calf serum (Atlanta Biologicals, Flowery Branch, Ga.), 1×MEM non-essential amino acids (Corning Life Sciences), and 1×pen/strep (Corning Life Sciences). Jurkat T cell leukemia and Ramos B cell lymphoma cell lines were cultured in RPMI1640 (Corning Life Sciences) supplemented with 10% fetal calf serum and 1× pen/strep. M21 cells were generously provided by Dr. Susan Knox (Stanford University). A375 cells and Ramos cells were obtained from ATCC (Manassas, Va.). Anti-CD3-APC-Cy7, anti-CD3-PerCP, anti-CD4-PE-Cy7, anti-CD8-BV785, anti-CD8-APC-Cy7, anti-CD19-BV421, anti-CD19-APC-Cy7, anti-CD25-PerCP-Cy5.5, anti-CD34-BV421, anti-CD69-BV650, anti-CD137-PE, anti-DYKDDDDK (FLAG)-PE, anti-DYKDDDDK (FLAG)-APC, anti-IFNγ-PB, anti-GD2-PE, mouse IgG2a,κ-PE isotype, and anti-rabbit IgG-PE were purchased from Biolegend (San Diego, Calif.) or BD Biosciences (San Diego, Calif.). Anti-TNFα-PE was purchased from eBioscience (San Diego, Calif.).

Blood Donors and PBMC Isolation

Blood was collected from consented donors in accordance with University of Kansas Medical Center IRB approved protocols. PBMCs where isolated using SepMate™ tubes (STEMCELL Technologies, Cambridge, Mass.) and Ficoll-Paque PLUS (GE Healthcare Life Sciences, Pittsburgh, Pa.) according to the manufactures' instructions. Cells were maintained in AIM V media (Thermo Fischer Scientific, Waltham, Mass.) supplemented with 2% human serum (Atlanta Biologicals, Atlanta, Ga.) and 20 ng/mL rhIL-2 (PeproTech, Rocky Hill, N.J.).

Retroviral Production

Retrovirus was produced by co-transfecting HEK 293T cells with CAR-encoding transfer plasmid, Peg-Pam-e plasmid encoding the MoMLV gag-pol, and the RDF plasmid encoding the RD114 envelope protein, in the presence of FuGENE® HD Transfection Reagent (Promega, Madison, Wis.). Retroviral supernatants were collected at 48 and 72 hours, purified through 0.45 µM filters, flash frozen in liquid nitrogen, and stored at −80° C.

T Cell Transduction and Isolation

T cells from freshly isolated PBMCs were activated for 3 days using 10 ng/mL anti-CD3ε clone OKT3 (BioXCell, Lebanon, N.H.) in complete AIM V media as previously described in Lamers C H, Willemsen R A, Luider B A, Debets R, Bolhuis R L. Protocol for gene transduction and expansion of human T lymphocytes for clinical immuno-gene therapy of cancer. Cancer Gene Ther. 2002; 9(7):613-23. For both primary and Jurkat T cell transduction, retroviral supernatants were bound to RETRONECTIN® (Takara Bio, Inc.) coated 6 well plates according to the manufacturer's instructions followed by addition of 2.5×10$^6$ Jurkat or activated primary T cells per well. After 48 hours, transduced cells were isolated using IMag™ anti-human CD19 magnetic beads (BD Biosciences, San Jose, Calif.) and expanded for 4 to 6 days before use in experiments. For some experiments, CD8$^+$ T cells were isolated by negative selection using anti-human CD4 IMag™ beads (BD Biosciences).

Phosphorylation Assay

Transduced Jurkat T Cells were washed in RPMI media and re-suspended at 5×10$^6$ cells/mL in RPMI media. For each treatment, 50 µL of T cells were transferred to a 96-well-round bottom plate and rested for one hour at 37° C. T cells were stimulated by addition of 50 RPMI media warmed to 37° C. containing either 2 µg/mL anti-CD3, 2.5×10$^5$ M21 or HeLa cells, or media alone. After 15 minutes, cells were fixed by addition of 100 µL 4% paraformaldehyde and incubated 10 minutes at 37° C. Cells were then labeled with anti-CD19 and anti-FLAG, permeabilized in ice-cold 90% methanol for 30 minutes, and stained intracellularly with anti-phospho-Erk1/2 (clone D13.14.4E, Cell Signaling Technology, Danvers, Mass.) followed by secondary staining with anti-rabbit Ig-PE and analyzed by flow cytometry.

Activation Assay

RPMI or AimV media were used for Jurkat or primary T cells respectively. Cells were washed in media and re-suspended at 2×10$^6$ cells/mL in media. For each treatment, 100 µL of cells were transferred to a 96-well flat-bottom plate and stimulated by the addition of 100 µL media containing either 2 µg/mL anti-CD3 (clone OKT3) (BioXcell), 2.0×10⁵ tumor cells, or media alone. Cells were then incubated for 24 hours at 37° C. with 5% $CO_2$. Following incubation, cells were pelleted by centrifuging at 400 g for 5 minutes. For primary T cells, 150 µL, of supernatant removed for CBA assays. Jurkat T cells were labeled with antibodies against CD3, CD69, and CD19. Primary T cells were labeled with antibodies against CD3, CD4, CD8, CD25, CD69, CD137, and either CD19 or CD34. All cells were analyzed by flow cytometry.

Lamp-1 Assay and Intracellular Staining

Transduced T cells were washed in AIM V media and re-suspended at 5×10⁶ cells/mL in AIM V containing 40 µL/mL anti-CD107a-BV605 antibody (Biolegend, San Diego, Calif.). For each treatment, 50 µL of T cells (2.5×10⁵ total) were transferred to a 96-well round-bottom plate and stimulated by addition of 50 µL AIM V media containing either 2 µg/mL anti-CD3, 20 ng/mL PMA and 1 µg/mL ionomycin, 2.5×10⁵ of the indicated tumor cells, or media alone. Cells were incubated one hour at 37° C. with 5% $CO_2$ before 20 µL of AIM V media containing GolgiStop™ (1.33 µL/mL final concentration, BD Biosciences) and Brefeldin A (3 µg/mL final concentration) was added to each well. Four hours later, cells were surfaced labeled with antibodies against CD3, CD4, CD8, and either CD19 or CD34 followed by intracellular staining with anti-TNF and anti-IFNγ. Cells were analyzed by flow cytometry.

Cytokine Bead Array

Cytokines were measured in supernatants collected from the 24-hour activation assays using a TH1/2/17 Cytokine Bead Array kit (BD Biosciences) according to the manufacturer's instructions. Samples were collected via flow cytometry and analyzed using FCAP Array 3.0 software (Soft Flow, Hungary).

Cytotoxicity Assay

Luciferase expressing M21, A375, HeLa, and Ramos tumor cells were generated by transduction with a retrovirus containing a luciferase transgene and a neomycin selection cassette. Transduced cells were selected by culturing in complete DMEM or complete RPMI supplemented with 400 µg/mL Geneticin (Life Technologies). To measure cytotoxicity, 2×10³ target cells were co-cultured in round bottom plates with effector cells at effector to target ratios ranging from 40:1 to 1:1 in AIM V media for 4, 8, and 24 hours. At the indicated time points, cells were gently mixed, pelleted at 400 g for 5 minutes, supernatants discarded, and re-suspended in luciferin lysis buffer, a process described in Siebring-van Olst E, Vermeulen C, de Menezes R X, Howell M, Smit E F, van Beusechem V W. Affordable luciferase reporter assay for cell-based high-throughput screening. J Biomol Screen. 2013; 18(4):453-61. After five min, luciferase activity was measured on a Synergy™ H1 plate reader and analyzed using Gen5 software (Biotek). Percent lysis was calculated using the formula: (Target Cells Plated–Target Cells Remaining)/Target Cells Plated×100 and percent specific lysis was normalized to ΔCD19 or ΔCD34 controls.

Flow Cytometry

Flow cytometry was performed using an LSRII (BD Biosciences). Unless otherwise noted, surface labeling was done in FACS buffer (2% FBS in PBS) in the dark at 4° C. for 20 minutes. Cells were then quenched in ice cold FACS buffer followed by two washes in FACS buffer and then fixed in 1% paraformaldehyde before analysis. For intracellular staining, surface labeled and fixed cells were permeabilized in 1× Permeabilization Buffer (eBioscience, San Diego, Calif.) followed by staining in Permeabilization Buffer at room temperature for 30 minutes. Cells were then washed three times in Permeabilization Buffer and re-suspended in FACS buffer for analysis.

Statistical Analysis

Statistical Analysis was performed using GraphPad Prism 7.0 (GraphPad Software, La Jolla, Calif.). Significance was determined using a one-way analysis of variance with post-hoc Tukey Test. Outliers were eliminated using the ROUT method (Q=0.1%).

Example 1

TCR-Based CAR Constructs

To generate a novel CAR that merges the antigen recognition capacity of currently used CARs with the functionality of the endogenous TCR complex, a scFv was fused to the constant region of TCRβ or TCRα. The scFv was based on the humanized anti-disialoganglioside (GD2) clone 3F8 and contained an embedded FLAG epitope tag to allow for detection of CAR surface expression. Each scFv-TCR chain was co-expressed with the constant region of the opposing TCR chain to create TCRαβ-CAR and TCRβα-CAR (FIG. 1A). To avoid mispairing with endogenous TCR chains, a second disulfide bond was added between the TCRα and TCRβ chains, which can be achieved by adding a single cysteine on each receptor chain to promote the formation of an additional interchain disulfide bond. For comparison, first and second generation CARs were also generated (FIG. 1A). As a marker for transduction, each construct also contained cDNA encoding the extracellular and transmembrane domains of CD19 (ΔCD19) attached via a 2A linker sequence.

Example 2

Surface Expression of TCR-Based CARs

Figure 2A:
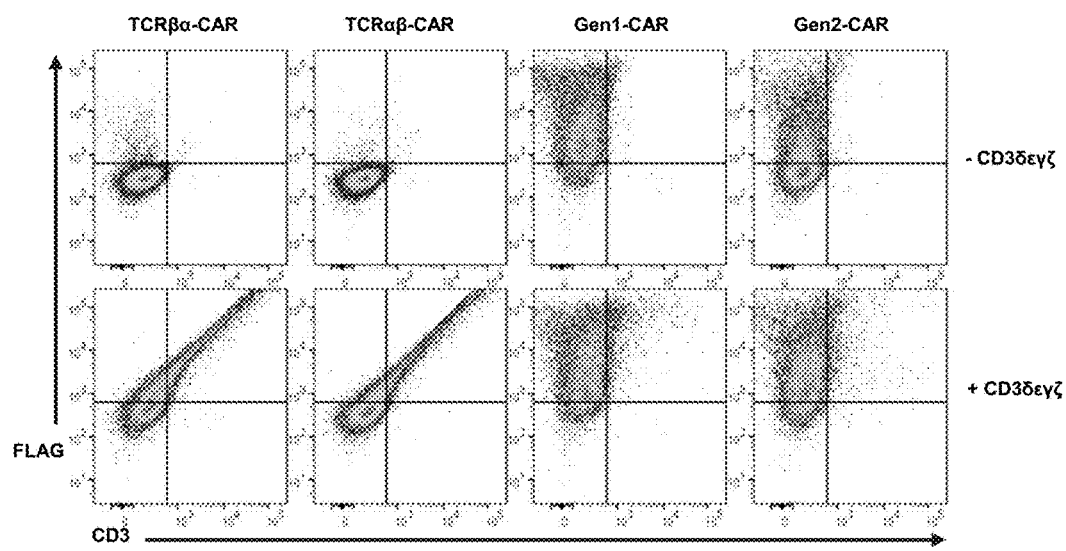
FIG. 2A shows a graph illustrating HEK 293T cells transfected with the indicated CAR only (top panel) or co-transfected with CD3δ, CD3ε, CD3γ, and CD3ζ (bottom panel).

The biochemical structure of the TCR complex prohibits the surface expression of individual chains, so each CAR was tested to determine whether it was dependent on CD3 for surface expression. HEK 293T cells were transfected with cDNA encoding each CAR alone or co-transfected with cDNA encoding CD3ϵ, CD3δ, CD3γ, and CD3ζ (FIG. 2A). Gen1-CAR and gen2-CAR could be detected on the cell surface independently of the CD3 chains. By contrast, TCRαβ-CAR and TCRβα-CAR could only be detected on the cell surface if the CD3 chains were co-expressed, demonstrating that the TCR-based CARs are incorporated into the endogenous TCR complex.

Figure 2B:
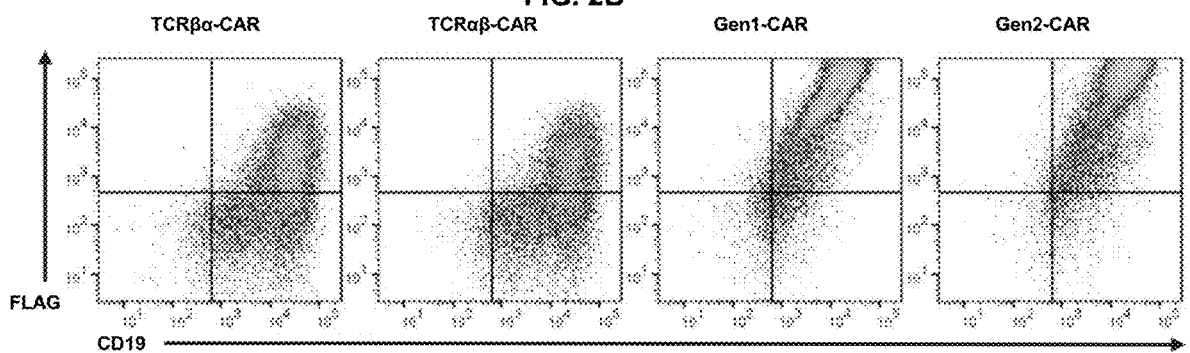
FIG. 2B depicts a graph illustrating the effect of transducing Primary T cells with the indicated CAR on the surface expression of FLAG and CD19.

Since T cells tightly regulate CD3 expression, surface expression of TCR-based CARs was hypothesized to be constrained by the availability of CD3, whereas surface expression of both gen1-CAR and gen2-CAR would be unrestricted in T cells. Indeed, primary human T cells transduced with the TCR-based CARs had significantly lower levels of CAR expression than T cells expressing gen1-CAR or gen2-CAR, despite similar surface expression of ΔCD19 (FIG. 2B).

Example 3

T Cell Activation by TCR-Based CARs

Figure 3:
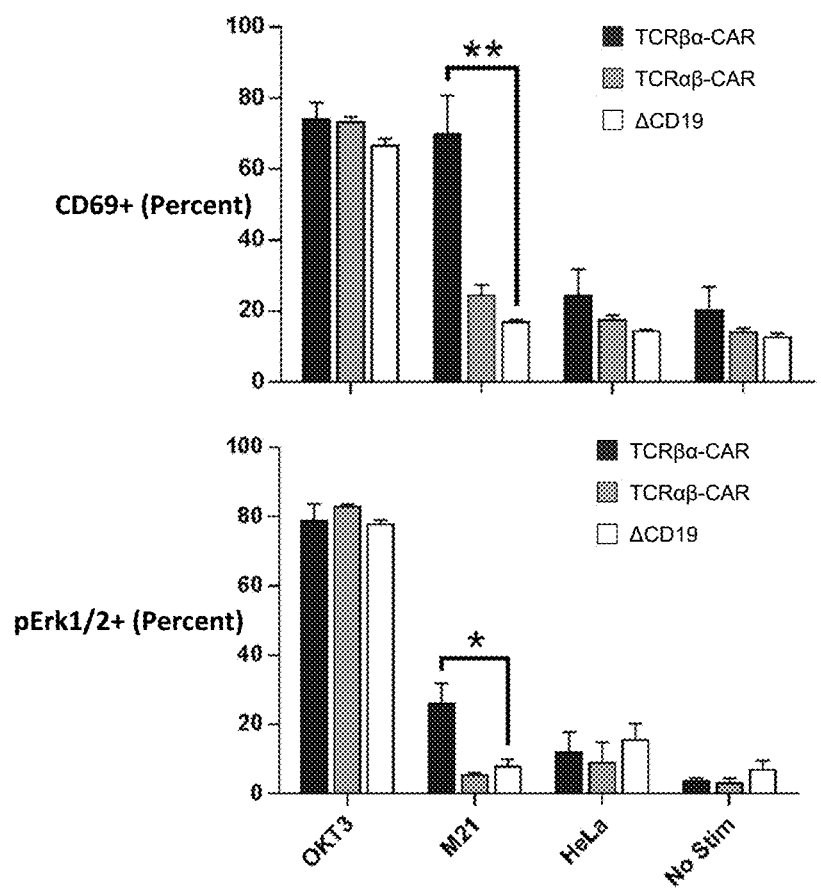
FIG. 3 depicts graphs illustrating the effect of transducing Jurkat T cells with the indicated construct and stimulating them as shown, with the percentages (mean±S.E.M.) of CD19+ cells expressing CD69 or phosphorylated ERK ($*p<0.05$, $****p<0.0001$, n=2-3).
Figure 9A:
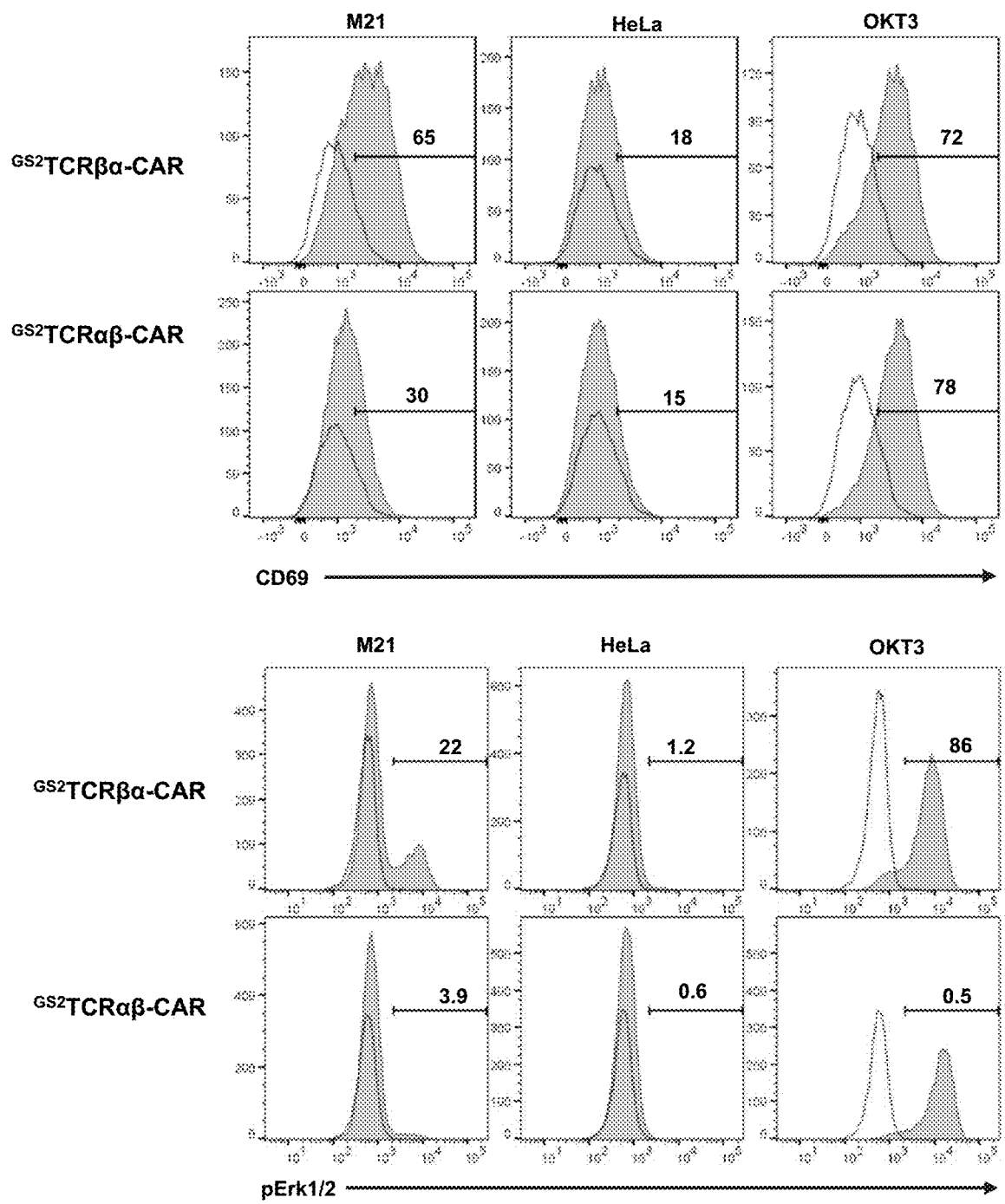
FIG. 9A shows graphs depicting data and a summary (mean±S.E.M.) of replicates for CD69 expression.

To test whether the TCR-based CARs could be used to activate T cells, TCRβα-CAR and TCRαβ-CAR were expressed in Jurkat T cells. As a negative control, a cell line was generated expressing the ΔCD19 empty vector. Cells were stimulated with anti-CD3ε, GD2$^{hi}$ M21 melanoma cells, GD2$^-$ HeLa cells, or left unstimulated. M21 cells could induce both CD69 expression and ERK1/2 phosphorylation in TCRβα-CAR T cells, but not TCRαβ-CAR T cells or ΔCD19 T cells (FIG. 3). Because directly fusing the scFv to the TCR could constrain the orientation of the scFv, constructs were generated in which a flexible (Gly$_4$Ser)$_3$ linker was inserted between the scFv and the TCR constant region. Addition of the linker did not affect T cell activation for either TCR-CAR construct (FIGS. 9A and 9B). These data indicate that TCR-CAR functionality is dependent on the scFv being fused to TCRβ and the presence of the (Gly$_4$Ser)$_3$ linker did not affect activity. Based on these results, the remaining studies were limited to the TCRβα-CAR construct.

Example 4

TCRβα-CAR-Induced Activation of Primary CD8$^+$ T Cells

Figure 4:
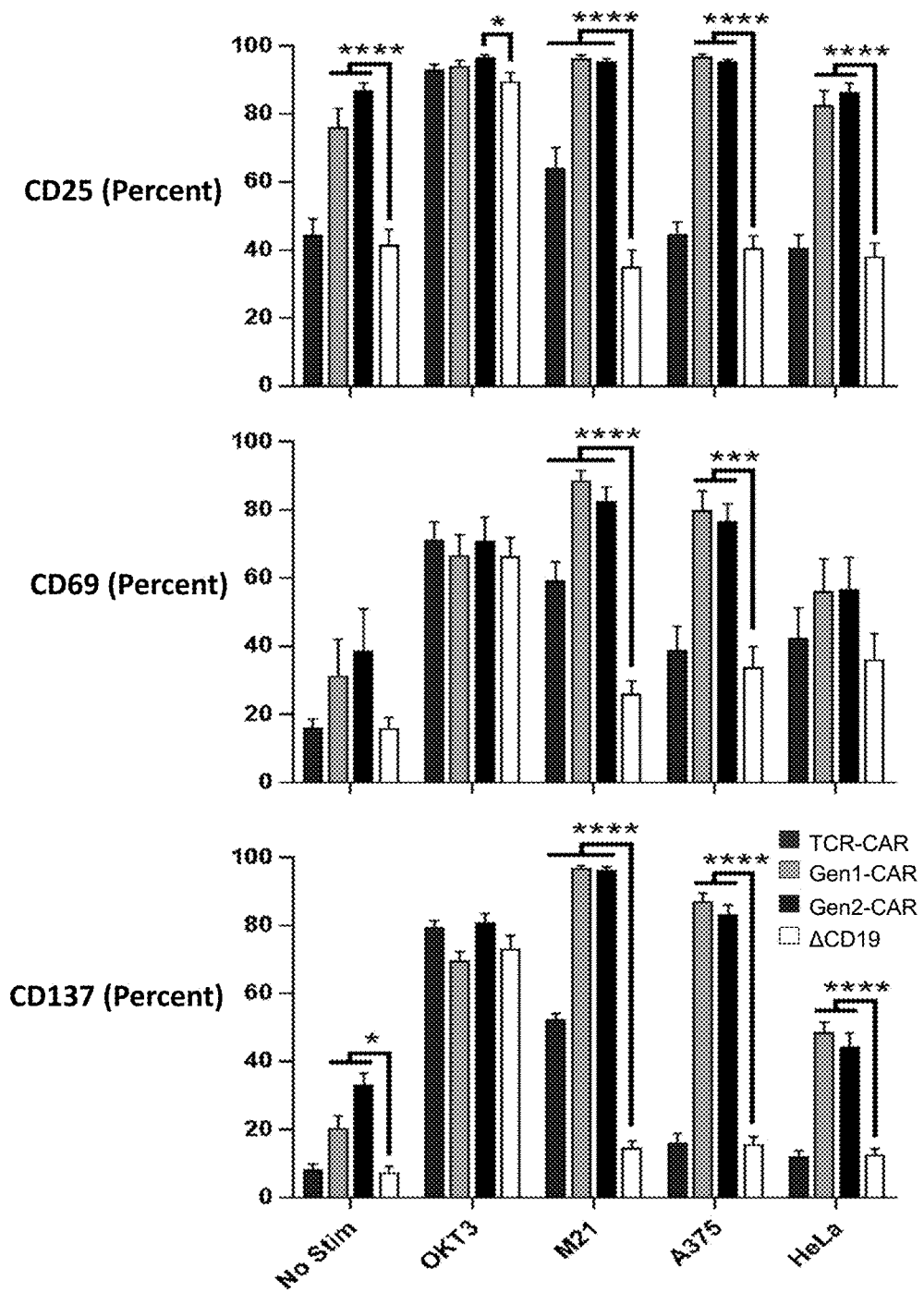
FIG. 4 depicts graphs illustrating the effect of transducing Primary T cells with the indicated constructs and stimulating them with the agents shown. Cells were gated on CD8$^+$ CD19$^+$ singlets and the percentages (mean±S.E.M.) of cells expressing CD25, CD69, and CD137 are shown ($p<0.01$, $*p<0.001$, $****p<0.0001$, n=6-8).
Figure 10A:
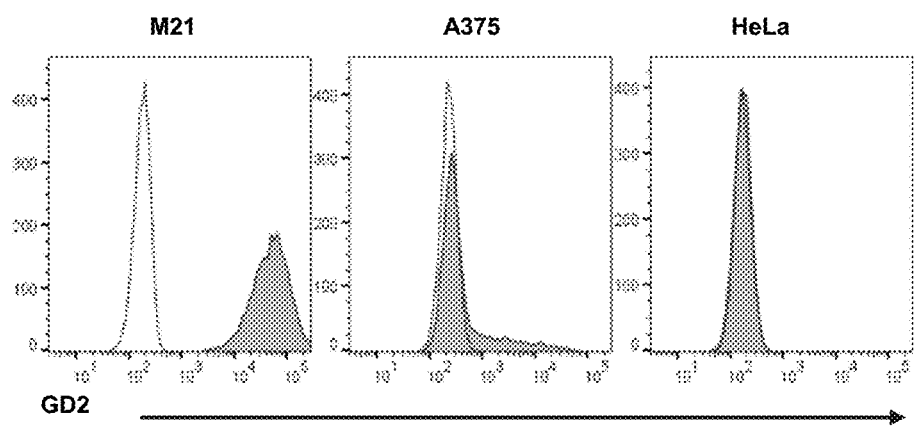
FIG. 10A shows graphs depicting GD2 expression on M21, A375, and HeLa cells, with each cell line labelled with anti-GD2 (shaded histograms) or an isotype control (dotted histograms).
Figure 10B:
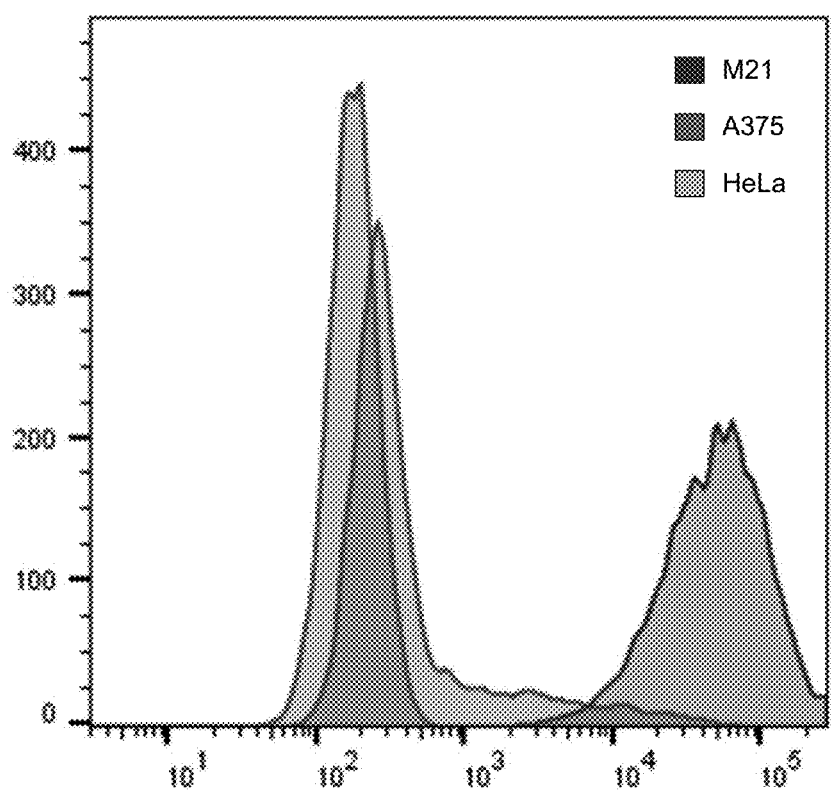
FIG. 10B shows a graph depicting the data from FIG. 10A presented as an overlay to show the differences in expression between M21, A375, and HeLa.

To test whether TCRβα-CAR T cells could discriminate between cells expressing varying levels of antigen, primary human T cells were transduced with TCRβα-CAR, gen1-CAR, gen2-CAR, or ΔCD19 and stimulated by co-culturing with GD2$^{hi}$ M21, GD2$^{lo}$ A375, or GD2$^-$ HeLa cells (FIGS. 10A and 10B). M21 cells induced expression of CD25, CD69, and CD137 in T cells expressing each CAR (FIG. 4), indicating that all three CARs could become activated in response to a GD2$^{hi}$ tumor cell line. A375 cells induced robust activation of gen1-CAR T cells and gen2-CAR T cells, but not TCRβα-CAR T cells. Even without stimulation, more gen1-CAR T cells and gen2-CAR T cells expressed CD25 and CD137 than TCRβα-CAR and ΔCD19 T cells ($p<0.05$). Collectively, these data indicate that TCRβα-CAR T cells can be activated in the presence of GD2$^{hi}$ tumor cells, but not GD2$^{lo}$ or GD2$^-$ tumor cells. Further, gen1-CAR and gen2-CAR result in non-specific T cell activation.

The finding that TCRβα-CAR T cells, but not gen1-CAR T cells or gen2-CAR T cells, could discriminate between cells expressing high and low levels of antigen is significant because tumor antigens are rarely expressed exclusively on tumor cells. Instead, tumor antigens are often highly expressed on tumor cells and at low levels on healthy cells. The on-target/off-tumor destruction of healthy tissue by CAR T cells is a common problem and can be lethal. Thus, the selectivity of TCRβα-CAR T cells for high antigen expression could prove to be a valuable safety feature.

Example 5

TCRβα-CAR CD8$^+$ T Cell Functionality

Figure 5:
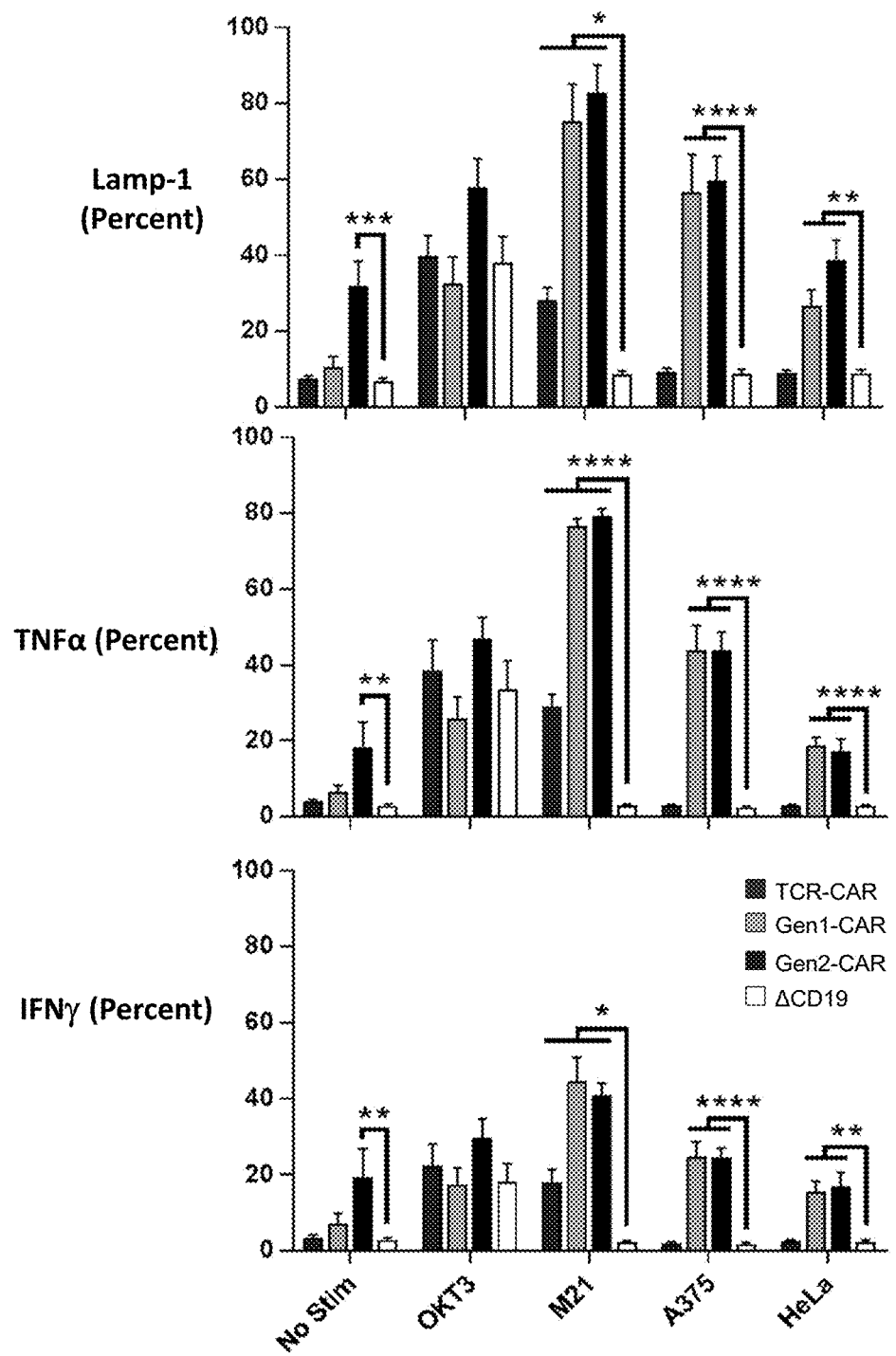
FIG. 5 depicts graphs illustrating the effects of transducing Primary T cells with the indicated construct and culturing them with no stimulation, anti-CD3, or the indicated cell line. Cells were gated on CD8+CD19+ singlets and the percentages (mean±S.E.M.) of cells expressing surface LAMP-1 or intracellular IFNγ and TNF shown ($*p<0.05$, $*p M 0.001$, $**p<0.0001$, n=5-8).

CD8$^+$ T cells expressing each CAR were stimulated with OKT3, M21, A375, or HeLa cells with non-stimulated (No Stim) cells as a control and assessed for their potential to degranulate and produce TNF and IFNγ (FIG. 5). After co-culturing with M21 cells, 28±3.1% of TCRβα-CAR CD8$^+$ T cells expressed surface LAMP1, 29±3.3% expressed TNF, and 18±3.3% expressed IFNγ ($p<0.05$, compared to M21-stimulated ΔCD19 T cells). As with the activation markers, TCRβα-CAR T cells did not express LAMP1, TNF, or IFNγ after culturing with A375 or HeLa cells.

After culturing with M21 and A375 cells, 75±9.7% and 57%±9.9%, of gen1-CAR T cells expressed surface LAMP1 respectively ($p<0.0001$, as compared to similarly activated ΔCD19 cells). Similarly, 89±3.8% and 60±6.4% of gen2-CAR T cells expressed surface LAMP1 after culturing with M21 and A375 cells, respectively ($p<0.0001$, as compared to ΔCD19 cells). Even in the presence of HeLa cells, 27%±4.3% of gen1-CAR T cells and 39%±5.2% of gen2-CAR T cells expressed LAMP1 as compared to 9.1±0.78% for TCRβα-CAR T cells ($p<0.01$) (FIG. 5). Similar trends were observed for both TNF and IFNγ expression by gen1-CAR and gen2-CAR T cells. Additionally, unstimulated gen2-CAR T cells exhibited significantly higher basal expression of LAMP1 ($p=0.0002$), TNF ($p=0.0015$), and IFNγ ($p=0.0068$) compared to ΔCD19 T cells.

Example 6

Cytokine Production by TCRβα-CAR T Cells

Figure 6:
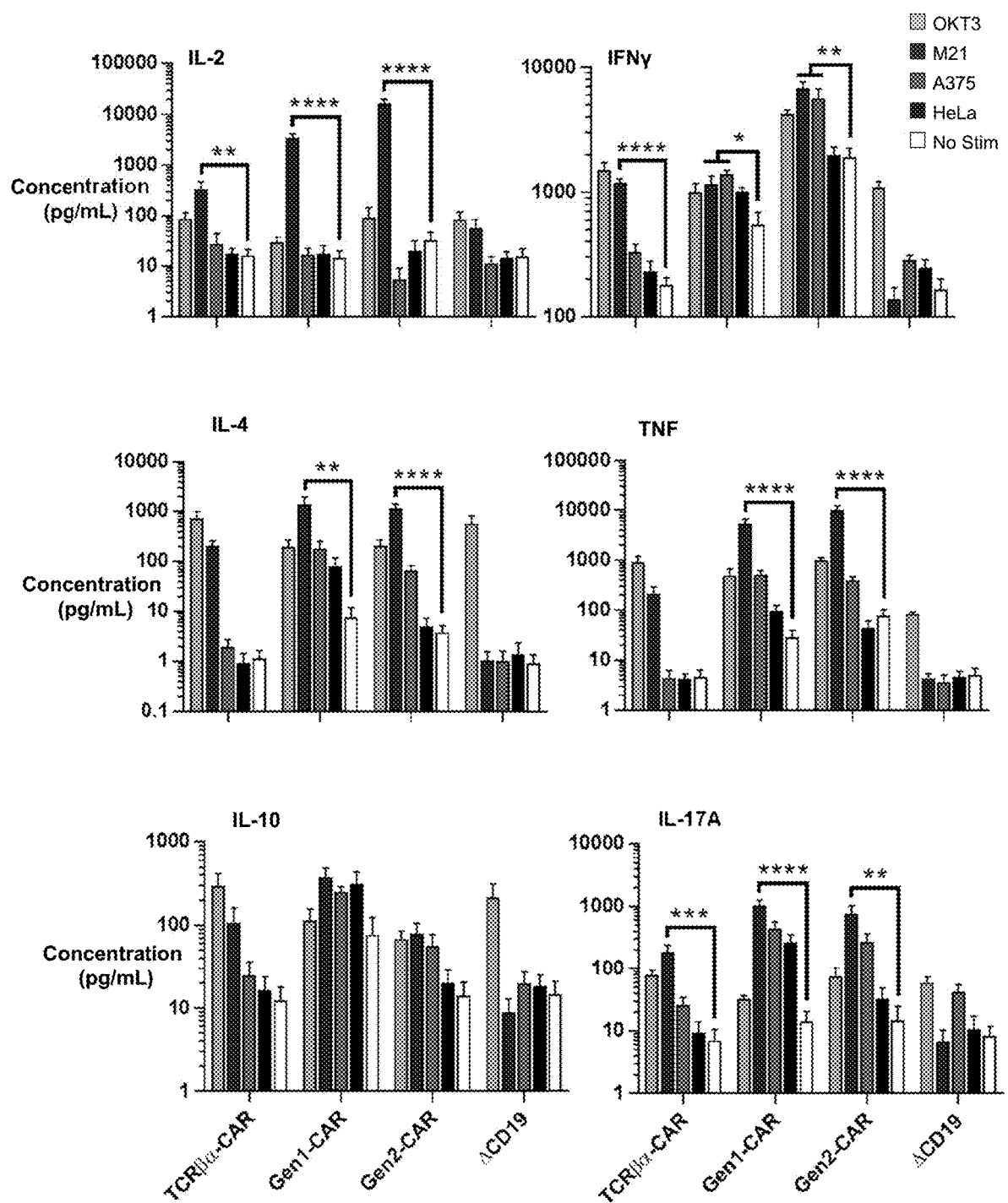
FIG. 6 depicts graphs illustrating the concentrations of each cytokine (mean±S.E.M.) produced after 24 hours by transducing Primary T cells with the indicated construct and culturing them with no stimulation, anti-CD3, or the indicated cell line ($*p<0.05$, $p<0.01$, $*p<0.001$, $****p<0.0001$, n=5-8).

Primary human T cells were transduced with each CAR, stimulated overnight with M21, A375, or HeLa cells, and analyzed for the production of the Th1 cytokines (IL-2, IFNγ, and TNF), Th2 cytokines (IL-4 and IL-10), and IL-17 (FIG. 6). In response to M21 cells, T cells expressing each CAR produced significantly more IL-2 compared to unstimulated cells, but gen1-CAR and gen2-CAR T cells produced 10-fold and 48-fold more IL-2 than TCRβα-CAR T cells. None of the CAR T cells produced IL-2 after co-culturing with A375 or HeLa cells.

TCRβα-CAR T cells produced IFNγ after co-culturing with M21 cells, but not with A375 or HeLa cells. By contrast, gen1-CAR and gen2-CAR T cells produced IFNγ in response to both M21 and A375 cells. The quantity of IFNγ produced by M21-stimulated gen2-CAR T cells was nearly 6-fold more than TCRβα-CAR T cells ($p<0.0001$). M21-stimulated gen1-CAR and gen2-CAR T cells also produced 25- and 47-fold more TNF, respectively, than M21-stimulated TCRβα-CAR T cells ($p<0.05$). Basal IFNγ and TNF production was similar between TCRβα-CAR and ΔCD19 T cells, but resting gen2-CAR T cells produced 12-fold more IFNγ and 15-fold more TNF than ΔCD19 T cells ($p<0.01$).

IL-4 production mirrored that of TNF for all CARs tested with only M21 stimulated gen1-CAR and gen2-CAR T cells resulting in statistically significant increases in IL-4 ($p=0.0027$ and $p<0.0001$, compared to unstimulated cells). Moreover, co-culture with M21 cells resulted in 6-fold ($p<0.0595$) and 5-fold more ($p=0.1444$) IL-4 produced by gen1-CAR T cells and gen2-CAR T cells, respectively, than M21 stimulated TCRβα-CAR T cells. No significant differences in IL-10 were observed for any of the CAR T cells for any stimulation though all CAR T cells produce IL-10 following M21 stimulation. Lastly, each CAR induced IL-17A production after co-culture with M21 cells, but was nearly 6-fold greater in gen1-CAR T cells ($p=0.012$) and 4-fold greater in gen2-CAR T cells ($p=0.0975$) than TCRβα-CAR T cells.

In summary, TCRβα-CAR T cells secreted IL-2, IFNγ, and IL-17 upon stimulation with GD2$^{hi}$ tumor cells, but not GD2$^{lo}$ or GD2$^{hi}$ cells. Gen1-CAR T cells and gen2-CAR T cells also produced these cytokines, but secreted significantly greater quantities and responded to both GD2$^{hi}$ and GD2$^{lo}$ cells. Additionally, stimulated gen1-CAR T cells and gen2-CAR T cells secreted TNF and IL-4 in significantly greater quantity than TCRβα-CAR.

In addition to being selectively activated by cells expressing high levels of antigen, another major difference between TCRβα-CAR and the other CARs was in the quantity of cytokines generated, particularly the pro-inflammatory cytokines (FIG. 6). In each case, production of cytokines by gen1-CAR T cells and gen2-CAR T cells greatly exceeded that of TCRβα-CAR T cells. While the production of large quantities of pro-inflammatory cytokines might be considered a positive attribute for anti-tumor immunity, it can be detrimental. IFNγ, TNF, and IL-17 can all be linked to CRS, a common phenomenon observed in patients receiving CAR therapy. Additionally, these cytokines can drive tumor proliferation and differentiation in the tumor microenvironment. Lastly, high expression of IL-2 by CAR T cells has been linked to the recruitment of regulatory T cells, which suppress CAR T cell activity by supporting the immunosuppressive tumor micro-environment. Thus, while the overall cytokine profile generated by all CARs we tested was skewed toward a Th1-like response, the more physiologic cytokines levels produced by TCRβα-CAR T cells is preferable in the treatment of solid tumors while also reducing the risk of CRS in patients receiving CAR immunotherapy.

Example 7

Antigen-Specific Cytotoxicity of TCRβα-CAR CD8+ T Cells

Total T cells were co-cultured expressing each CAR with M21 (FIG. 7A) or HeLa cells (FIG. 7B). All CAR constructs induced cytotoxicity of M21 cells in a dose-dependent manner and none of the constructs targeted the HeLa cells. Next, the cytotoxic potential of purified CAR-expressing CD8$^+$ T cells were examined at three time points (FIG. 7C-E). At each time point, TCRβα-CAR, gen1-CAR, and gen2-CAR T cells induced cytolysis of M21 cells and the cytolysis was complete for all CARs within 24 hours. Gen1-CAR CD8$^+$ T cells and gen2-CAR CD8$^+$ T cells also targeted antigen negative HeLa cells whereas TCRβα-CAR CD8$^+$ T cells did not (FIG. 7F). These data demonstrate that TCRβα-CAR T cells could induce tumor cell lysis in an antigen-specific-manner.

Example 8

Targeting Other Antigens with TCRβα-CAR

Figure 8A:
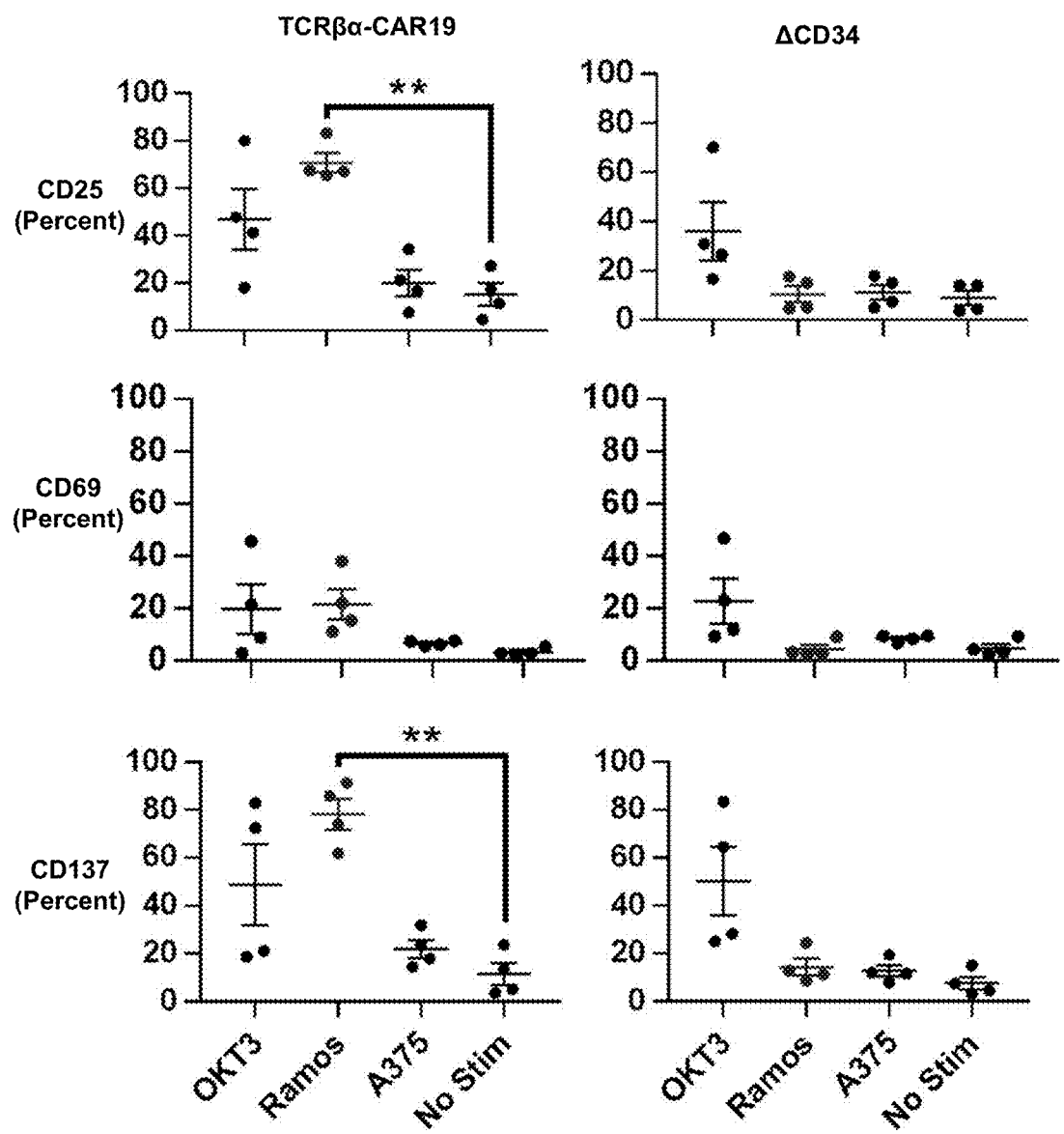
FIG. 8A shows graphs illustrating the effects of transducing Primary T cells with anti-CD19 TCRβα-CAR or ΔCD34 and incubating them under the indicated stimuli. Shown are the percentages (mean±S.E.M.) of cells expressing CD25, CD69, and CD137 (n=4).
Figure 8B:
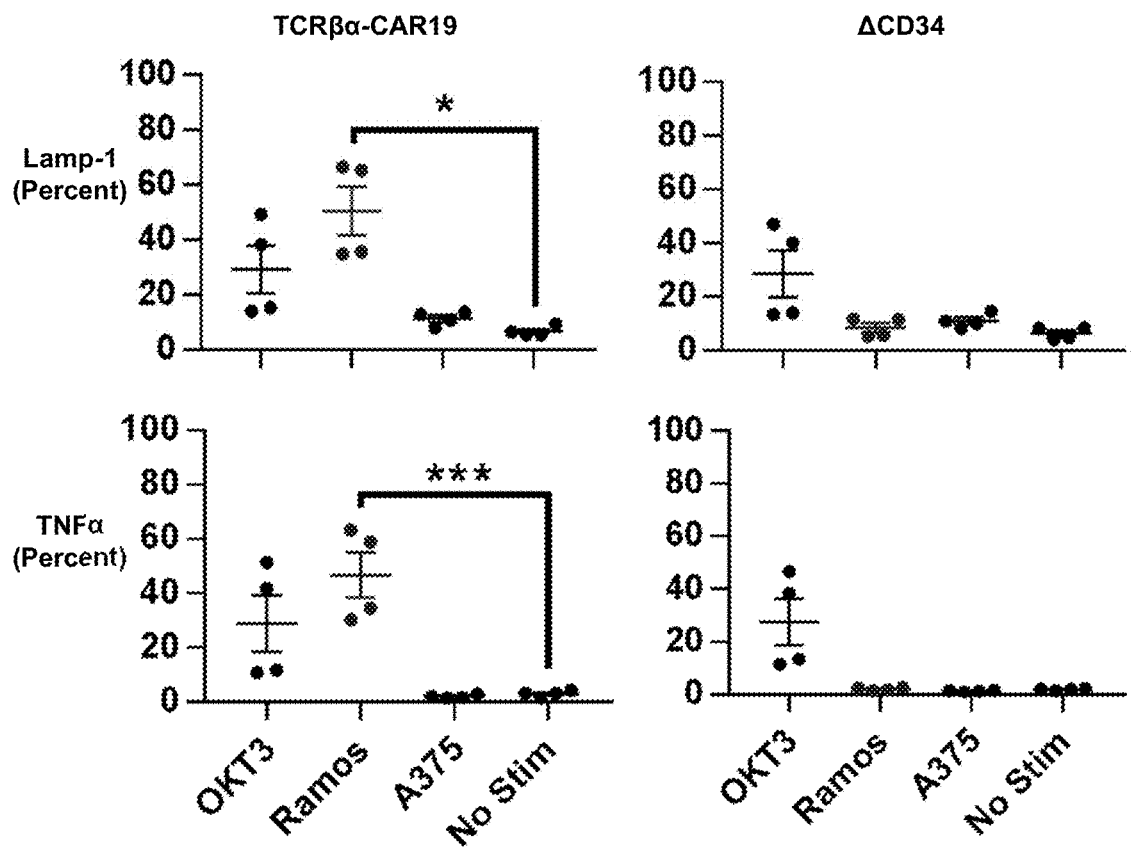
FIG. 8B shows graphs illustrating the effects of transducing Primary T cells with anti-CD19 TCRβα-CAR or ΔCD34 and incubating them under the indicated stimuli. Shown are the percentages (mean±S.E.M.) of cells expressing surface LAMP-1 or intracellular IFNγ and TNF (n=4).
Figure 8C:
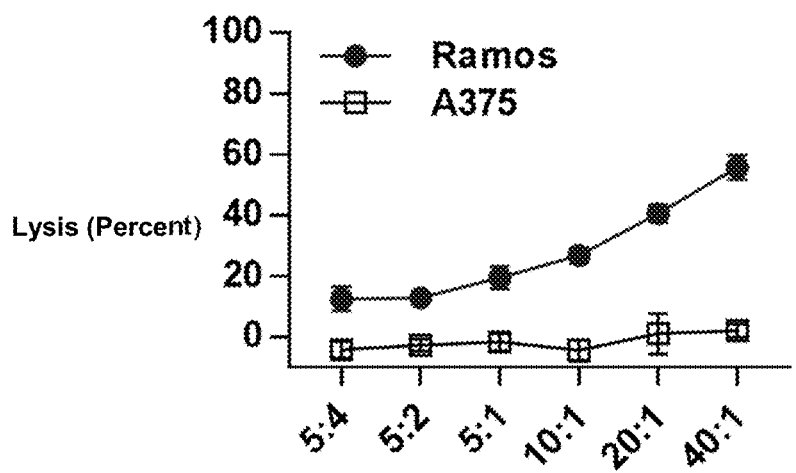
FIG. 8C shows a graph depicting the ability of anti-CD19 TCRβα-CAR T cells to lyse Ramos or A375 cells (n=4).

To test whether the novel CAR could induce T cell activity for other antigens, the anti-GD2 scFv were replaced with anti-CD19 scFv (as described in Nicholson I C, Lenton K A, Little D J, Decorso T, Lee F T, Scott A M, et al. Construction and characterisation of a functional CD19 specific single chain Fv fragment for immunotherapy of B lineage leukaemia and lymphoma. Mol Immunol. 1997; 34(16-17):1157-65.) to create TCRβα-CAR19. To avoid the anti-CD19 CAR from targeting ΔCD19-expressing CAR T cells, the ΔCD19 transduction marker were switched with a truncated CD34 (ΔCD34). After co-culturing with CD19$^+$ Ramos cells, but not CD19$^-$ A375 cells, TCRβα-CAR19 T cells expressed CD25, CD69, and CD137 (FIG. 8A). TCRβα-CAR19 CD8$^+$ T cells also had antigen-specific increases in intracellular TNF and surface LAMP1 expression (FIG. 8B). Lastly, TCRβα-CAR19 T cells could induce cytolysis of Ramos cells but demonstrated no cytotoxicity against antigen negative targets (FIG. 8C). Collectively, these data demonstrate that TCRβα-CAR is a flexible platform capable of targeting multiple antigen targets.

Example 9

Comparing the Functionality of T Cells Expressing TCR-CAR and Gen1-CAR

Human PBMCs will be transduced with TCR-CAR, gen1-CAR, or ΔCD19 empty vector control, by transfection with SFG plasmids containing cDNA encoding each CAR construct along, pRDF (contains RD114 retroviral envelope), and pPEG-Pam3 (which contains MoMLV gag-pol). Because the phenotype of the T cells changes over time, all assays will be performed within one week of transduction. Cells will be stimulated with GD2$^{hi}$ M21 cells, GD2$^{lo}$ A375 cells, GD2$^-$ HeLa cells, or anti-CD3ε.

At various time points ranging from 0-30 min after stimulation, cells will be fixed, surface labeled with anti-CD19 (to identify the transduced cells), anti-CD4, and anti-CD8. Then, cells will be permeabilized and labeled intracellularly with antibodies that recognize the phosphorylated forms of ZAP-70 (Tyr-319), LAT (Tyr-226), PLCγ1 (Tyr-783), and ERK (Thr-202/Tyr-204). As controls, we will use non-specific antibodies of the same isotype and antibodies against non-phosphorylated forms of the proteins.

cDNA were generated in which expression of Luc2P (Promega Corporation, Madison, Wis.) is under control of either the NF-AT or the NF-κB promoter. CAR-expressing T cells will be transduced with NFAT-Luc2P or NFκB-Luc2P and cultured with target cells for 0, 4, 8, or 18 hours and luciferase activity will be assessed using a microplate reader. The short half-life (~1h) of Luc2P allow meaningful data to be generated from this time course.

CAR-expressing cells will be cultured with target cells for 0, 24 or 48 hours. Tissue culture supernatant will be collected to quantify the production of Th1, Th2, and Th17 cytokines (IL-2, IL-4, IL-17A, IFNγ, and TNFα) by ELISA. In addition, cells will be assessed for their expression of the activation markers CD69 and CD25 and the transcription factors T-bet, GATA-3, and RORγt.

Example 10

Comparing the Functionality of TCR/41BBL-CAR and a Gen2-CAR cDNA will be generated encoding a secreted form of 4-1BBL fused to the same scFv as TCR-CAR and gen2-CAR. Expression of scFv-4/1BBL will be under control of the NF-AT promoter. For example, in some experiments, SEQ ID NO: 26 encoding SEQ ID NO: 25 can be used which encodes anti-GD2 scFv-HA-4-1BBL. The complete construct will be TCRα-2A-scFv/TCRβ-STOP-NFAT promoter-scFv-4-1BBL (SEQ ID NO: 41, TCR/41BBL-CAR) and will be used as follows:

Using the NF-AT promoter to express scFv-4-1BBL: Jurkat T cells will be transduced with TCR/41BBL-CAR and stimulated with anti-CD3ε. One and two days later, tissue culture supernatant will be used to label M21 cells or HeLa cells. The ability of secreted scFv-4-1BBL to bind tumor cells will be assessed by flow cytometry using antibodies against an HA tag inserted into the cDNA encoding scFv-4-1BBL.

Inducing 4-1BBL-mediated T cell activation: TCR-CAR and TCR/41BBL-CAR-expressing primary T cells will be co-cultured with M21, A375, or HeLa cells for 0, 24, 48, and 72 hours. As a positive control, agonistic anti-4-1BBL antibodies will be added to the cells. Because 4-1BB promotes the expression of Bcl-xL, we will measure Bcl-xL expression in CAR-expressing T cells using intracellular staining and flow cytometry.

Comparing cytotoxicity and exhaustion in TCR/41BBL-CAR- and gen2-CAR-T cells: Cytotoxicity will be assessed by culturing CAR-expressing T cells with GFP+M21, GFP+A375, or GFP+ HeLa cells at effector to target ratios ranging from 0.5 to 8. Target cell lysis will be measured by loss of GFP+ cells, for example, by inducing cell death by a variety of apoptotic stimuli in various GFP-expressing mammalian cell lines, including those routinely used in anti-cancer drug screening. A decrease in fluorescence may be assessed either by flow cytometry (and compared with other apoptotic markers) or by a fluorescence microplate reader. Parallel cultures will be incubated for 0, 2, 4, or 7 days and monitored for expression of the activation markers CD25 and CD127 and the exhaustion markers and PD-1, LAG-3, and TIM-3.

Example 11

Efficacy of TCR/41BBL-CAR in an (NOD-SCID-$\gamma c^{-/-}$) NSG Mouse Tumor Mode NSG mice will be inoculated sc with $10^6$ firefly luciferase-expressing M21 cells. Tumor burden will be monitored with calipers and using in vivo imaging by injecting mice with D-luciferin and visualizing the tumor with an IVIS® Imaging System (PerkinElmer, Waltham, Mass.). When tumors reach an approximate volume of 100-200 $mm^3$, mice will be injected with $10^6$ T cells expressing TCR/41BBL-CAR, gen2-CAR, or ΔCD19 alone. Tumor growth will continue to be monitored bi-weekly for at least six weeks or until the tumor burden reaches 1.5 cm diameter. In addition, the number of CAR-expressing T cells in the blood will be monitored weekly by obtaining a droplet of blood and labeling the cells with antibodies against CD3, CD4, CD8, CD19, and FLAG and analyzing the cells using flow cytometry.

After euthanasia, lungs, liver, kidneys, and spleens will be weighed, harvested, and paraffin embedded for histopathology. In addition to bioluminescence imaging, tumor burden will be determined as was done previously. In brief, the area (in square micrometers) occupied by the tumor will be calculated from 15 200× randomly selected fields using the MetaMorph 7 image analysis system. Immunohistochemical staining with FLAG antibodies will be carried out to estimate numbers of infiltrating CAR cells. A portion of the spleen and lymph nodes will be collected so the T cells can be analyzed by flow cytometry for expression of the activation markers CD25 and CD69, the differentiation markers CD45RA, CD45RO, CD27, and CD11a, and the exhaustion markers PD-1, LAG-3, and TIM-3.

TCR/41BBL-CAR is hypothesized to destroy the tumor as completely as gen2-CAR, albeit with slower kinetics because of the more physiologic manner in which T cell activation will occur. Slower kinetics will likely lessen the cytokine release syndrome often observed when large numbers of T cells release cytokines simultaneously. Another advantage of slower activation kinetics is that the IFNγ and TNFα concentrations produced within the tumor are likely to be more physiologic, resulting in the conversion of tumor-infiltrating macrophages and neutrophils from pro-tumorigenic cells to pro-inflammatory cells. The activation of innate cells will be critical for complete tumor destruction in patients Despite the clinical success observed using 4-1BBL, it remains prudent to directly compare 4-1BBL to other co-receptors and combinations of co-receptors If TCR/41BBL-CAR does not reduce the tumor burden to the level observed with gen2-CAR, this would suggest that T cell activation is not being adequately induced by either signal 1 (TCR) or signal 2 (4-1BB). To test whether TCR ligation is sufficient to induce scFv-4-1BBL expression in vivo, the tumor model described here will be repeated except the scFv-4-1BBL cDNA will be replaced with cDNA encoding click beetle red luciferase. Green tumor cells and red T cells can be visualized simultaneously. If red luciferase are not detected in the tumors, then the TCR-CAR-induced signal is too weak to induce scFv-4-1BBL expression. Such a result would indicate that a different promoter is needed. In addition to the ideas discussed in Example 10, signals generated in the tumor microenvironment, such as those generated by IL-10 or TGFβ will also be exploited. IL-10 activates the STAT3 and TGFβ activates the SMAD complex, so the red luciferase assay will be repeated to determine whether activation can be detected of the either the STAT3 or SMAD transcriptional response elements in the tumor.

If red cells are observed in the tumor, the original experiment in this aim will be repeated and the tumor will be excised at a time at which CAR-expressing T cells infiltrate. The tumor will be examined for scFv-4-1BBL expression using anti-HA and immunohistochemistry to determine if the co-receptor ligand is expressed. The findings may show that scFv-4-1BBL is expressed adequately, but does not function in vivo. An alternate strategy for inducing 4-1BB signaling would be to drive expression of "constitutively active" 4-1BB through the NF-AT promoter. Because of the high level of constitutive activity of gen2-CAR, an option would be to drive expression of a gen2-CAR using the NF-AT promoter.

Example 12

Figure 11:
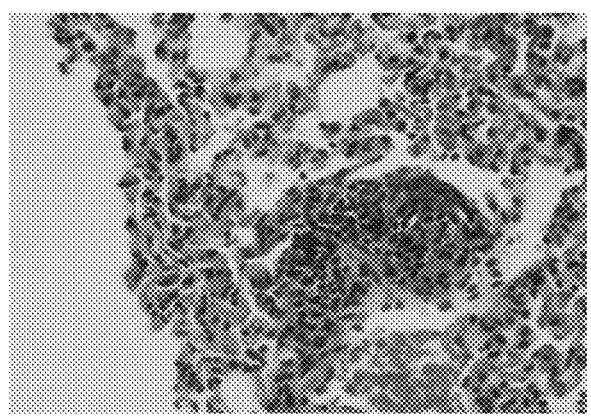
FIG. 11 depicts Hematoxylin and eosin staining of tumor cells in a mice lung after mice were tolerized against M21 cells in utero and reimplanted with M21 cells two weeks post-weaning.

TCR/41BBL-CAR Inducement of Tumor Destruction in a Novel Immunocompetent Murine Tumor Model In a paper currently in revision, immunocompetent mice were injected in utero with M21 cells to promote tolerance (FIG. 11). Postnatally, mice were reimplanted with luciferase-expressing M21 cells and tumors were found in the lung, a common site of metastasis in cancer patients. The ability of TCR/41BBL-CAR- and gen2-CAR-expressing murine T cells to destroy the tumors will be compared. Timed pregnant inbred FVB mice will be injected with Luc2-expressing M21 cells ($2.5 \times 10^4$) into the amniotic cavity. Two weeks post-weaning, mice will be transplanted with $10^6$ Luc2-expressing M21 cells via the tail vein. Fifty days later, splenocytes from syngeneic mice will be transduced with TCR/41BBL-CAR or gen2-CAR and infused into the tumor-bearing mice via retroorbital injection or via the lateral tail vein. Mice will be analyzed as described in aim 2a.

If TCR/41BBL-CAR does not reduce the tumor burden in immunocompetent mice, this would indicate that further CAR development is warranted. In particular, pro-inflammatory innate immune cells would need to be recruited. Adding components to the CARs that would manipulate the tumor microenvironment and skew macrophage and neutrophil differentiation will be investigated.

Example 13

Targeting One Antigen with the scFv Fused to TCR-CAR and a Different Antigen with the scFv Fused to 4-1BBL Stable M21 melanoma cell lines have been generated that express CD19 and luciferase. M21 cells also express high levels of the GD2 disialoganglioside. $CD19^+GD2^+M21$ cells will be used to test the model that it is possible to target one antigen with the scFv fused to TCR-CAR and a different antigen with the scFv fused to 4-1BBL. NOD.Cg-$Prkdc^{scid}Il2rg^{tm1Wjl/SzJ}$ (NSG) mice will be implanted with $2\times10^6$ M21 melanoma cells in Matrigel® subcutaneously into the flank. M21 cells express high levels of the GD2 antigen. An M21 variant cell line that expresses CD19 and luciferase was generated. One week after implantation, $5\times10^6$ TCR-CAR T cells will be injected retroorbitally into the mice. Mice will be imaged using an IVIS® in vivo imaging system prior to injection of CAR T cells and weekly thereafter. For in vivo imaging, mice will be injected intraperitoneally with luciferin, anesthetized, and scanned. The relative light units emitted from each mouse will be calculated at each time point. After 30 days, mice will be euthanized and the any remaining tumor will be excised and weighed. Mice will be withdrawn from study if the tumor reaches more than two cm3 or the body conditioning score (as defined in Lab Animal Sciences 49: 319) drops below two.

TABLE 1

CAR constructs used in the melanoma model

| Construct | TCR portion | 4-1BB portion |
|---|---|---|
| 1 | Anti-CD19 TCR-CAR | |
| 2 | Anti-CD19 TCR-CAR | Secreted Anti-GD2 scFv-41BBL fusion protein |
| 3 | Anti-CD19 TCR-CAR | 4-1BB signaling motif fused to the intracellular tail of truncated TCRα |
| 4 | Anti-CD19 TCR-CAR | 4-1BB signaling motif fused to the intracellular tail of truncated scFv-TCRβ |
| 5 | Anti-CD19 TCR-CAR | 4-1BB signaling motif fused to the intracellular tail of CD3δ |
| 6 | Anti-CD19 Gen1-CAR | |
| 7 | Anti-CD19 Gen1-CAR | Secreted Anti-GD2 scFv-41BBL fusion protein |
| 8 | Anti-CD19 Gen1-CAR | 4-1BB signaling motif fused to the intracellular tail of CD3δ |
| 9 | Anti-CD19 Gen2-CAR | |
| 10 | No CAR negative control | |

Example 14

Cytotoxic T Lymphocyte (CTL) Activity Assay

Luciferase-expressing M21 cells described above will be used in an in vitro CTL assay. Briefly, the scFv used for each construct listed in table 2 will target the GD2 antigen. Total T cells expressing each CAR will be incubated with M21 cells at T cell to M21 cell ratios of 5:4, 5:2, 10:1, 20:1, and 40:1. After four hours of co-culture, luciferase activity remaining in each well will be quantified and compared to the no CAR control. Specific CTL activity will be calculated by subtracting the luciferase activity of M21 cells plated with CAR T cells from the luciferase activity of M21 cells plated. The result will be divided by the luciferase activity of M21 cells plated, normalized to wells with CAR-deficient T cells and multiplied by 100.

TABLE 2

Constructs tested in vitro

| | |
|---|---|
| TCR-CAR | scFv directly fused to the constant region of TCRβ co-expressed with the constant region of TCRα |
| TCRβc-CAR | scFv directly fused to the constant region of TCRβ |
| TCRαc-CAR | scFv directly fused to the constant region of TCRα |
| TCRβc/TCRαc-CAR | scFv directly fused to the constant region of TCRβ co-expressed with scFv directly fused to the constant region of TCRα |
| TCRβ-CAR | scFv directly fused to full-length TCRβ |
| TCRα-CAR | scFv directly fused to full-length TCRα |
| TCRβ/TCRα-CAR | scFv directly fused to full-length TCRβ co-expressed with scFv fused to full-length TCRα |
| TCRβLL-CAR | scFv directly fused to full-length TCRβ via three consecutive gly-ser linker regions |
| TCRαLL-CAR | scFv directly fused to full-length TCRα via three consecutive gly-ser linker regions |
| TCRβLL/TCRαLL-CAR | scFv directly fused to full-length TCRβ via three consecutive gly-ser linker regions co-expressed with scFv fused to full-length TCRα via three consecutive gly-ser linker regions |
| No CAR control | |

What is claimed is:

1. A nucleic acid molecule encoding a chimeric antigen receptor, the chimeric antigen receptor comprising: a T-cell receptor beta chain constant region and a T-cell receptor alpha chain constant region, wherein the T-cell receptor beta chain constant region is fused to a single chain variable fragment (scFv) that specifically binds to a tumor specific antigen, wherein the chimeric antigen receptor does not include a T-cell receptor beta chain variable region and a T-cell alpha chain variable region, and wherein the T-cell receptor beta chain constant region is configured to complex with the T-cell receptor alpha chain constant region through a non-endogenous disulfide bond, wherein the non-endogenous disulfide bond (a) arises from introducing cysteine mutations in the T-cell receptor alpha chain constant region and the T-cell receptor beta chain constant region and (b) promotes pairing of exogenous T-cell receptor alpha chain constant region and T-cell receptor beta chain constant region, wherein the cysteine mutations in the T-cell receptor alpha chain constant region and the T-cell receptor beta chain constant region are T42C and S57C, respectively.

2. The nucleic acid molecule of claim 1, wherein the T-cell receptor beta chain constant region comprises an amino acid sequence of SEQ ID NO: 3.

3. The nucleic acid molecule of claim 1, wherein the T-cell receptor alpha chain constant region comprises an amino acid sequence of SEQ ID NO: 5.

4. The nucleic acid molecule of claim 1, wherein the tumor specific antigen is selected from the group consisting of disialoganglioside GD2 (GD2), mucin 1 (MUC1), prostate-specific membrane antigen (PSMA), human epidermal growth factor receptor 2 (Her2), mucin 16 (MUC16), melanoma-associated antigen 1(MAGE-A1), carbonic anhydrase 9 (CAIX), b-lymphocyte surface antigen CD19 (CD19), prominin-1 (CD133), CD33 antigen (CD33), CD38 antigen (CD38), neural cell adhesion molecule (CD56), interleukin-3 receptor (CD123), and b-lymphocyte antigen CD20 (CD20).

5. A modified T lymphocyte that comprises (a) a nucleic acid molecule according to claim 1 and (b) a nucleic acid molecule encoding a 4-1BB ligand (4-1BBL) fused to a scFv that specifically binds to a tumor-specific antigen.

6. The modified T lymphocyte of claim 5, wherein the nucleic acid molecule encoding the 4-1BBL fused to the scFv includes 4-1BBL that lacks its transmembrane domain.

7. The modified T lymphocyte of claim 5, wherein the nucleic acid molecule encoding the 4-1BBL fused to the scFv includes 4-1BBL that has a mutation in its trimerization domain.

8. The modified T lymphocyte of claim 5, wherein the nucleic acid molecule encoding the 4-1BBL fused to the scFv includes 4-1BBL that (i) lacks its transmembrane domain and (ii) has a mutation in its trimerization domain.

\* \* \* \* \*

SEQUENCE LISTING

<160> NUMBER OF SEQ ID NOS: 41

<210> SEQ ID NO 1
<211> LENGTH: 171
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Asp His
                165                 170

<210> SEQ ID NO 2
<211> LENGTH: 516
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
ttggacctgc ggcagggcat gttcgcccag ctggtggctc agaacgtgct gctgatcgac      60 ggcccctga gctggtactc tgatcctgga ctggctggcg tgtccctgac cggcggactg      120
agctacaaag aggacacaaa agaactggtg gtggccaagg ccggcgtgta ctacgtgttc      180
tttcagctgg aactgcggag agtggtggcc ggcgagggat ctggatctgt gtctctggcc      240
ctgcatctgc agccctgag atctgctgct ggcgcagctg ctctggctct gaccgtggat       300
ctgcctcctg ccagcagcga ggccagaaac agcgcattcg ggtttcaagg caggctgctg      360
cacctgagcg ccggacagag actgggagtg catctgcaca cagaggccag agccaggcac      420
gcctggcagc tgacacaggg cgctacagtg ctgggcctgt tcagagtgac ccccgagatt      480
cctgccggcc tgcctagccc tagaagcgac cactaa                                516

<210> SEQ ID NO 3
<211> LENGTH: 175
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 3

```
Val Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys
                165                 170                 175
```

<210> SEQ ID NO 4
<211> LENGTH: 525
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
gtcgacctga acaaggtgtt cccacccgag gtcgctgtgt ttgagccatc agaagcagag      60
atatcccaca cccaaaaggc cacactggtg tgcctggcca caggcttctt ccccgaccac     120
gtggagctga gctggtgggt gaatgggaag gaggtgcaca gtggggtctg cacggacccg     180
cagcccctca aggagcagcc cgccctcaat gactccagat actgcctgag cagccgcctg     240
agggtctcgg ccaccttctg gcagaacccc cgcaaccact tccgctgtca agtccagttc     300
tacgggctct cggagaatga cgagtggacc caggataggg ccaaaccgt cacccagatc      360 gtcagcgccg aggcctgggg tagagcagac tgtggcttta cctcggtgtc ctaccagcaa     420
ggggtcctgt ctgccaccat cctctatgag atcctgctag gaaggccac cctgtatgct      480 gtgctggtca gcgcccttgt gttgatggct atggtcaaga gaaag                     525
```

<210> SEQ ID NO 5
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Pro Ala Val Tyr Gln Leu Arg Asp Ser Lys Ser Ser Asp Lys Ser Val
1               5                   10                  15

Cys Leu Phe Thr Asp Phe Asp Ser Gln Thr Asn Val Ser Gln Ser Lys
            20                  25                  30

Asp Ser Asp Val Tyr Ile Thr Asp Lys Cys Val Leu Asp Met Arg Ser
        35                  40                  45

Met Asp Phe Lys Ser Asn Ser Ala Val Ala Trp Ser Asn Lys Ser Asp
    50                  55                  60

Phe Ala Cys Ala Asn Ala Phe Asn Asn Ser Ile Ile Pro Glu Asp Thr
65                  70                  75                  80

Phe Phe Pro Ser Pro Glu Ser Ser Cys Asp Val Lys Leu Val Glu Lys
                85                  90                  95

Ser Phe Glu Thr Asp Thr Asn Leu Asn Phe Gln Asn Leu Ser Val Ile
            100                 105                 110

Gly Phe Arg Ile Leu Leu Leu Lys Val Ala Gly Phe Asn Leu Leu Met
        115                 120                 125

Thr Leu Arg Leu Trp Ser Ser Ala
    130                 135
```

<210> SEQ ID NO 6
<211> LENGTH: 408
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
cctgccgtgt accagctgag agacagcaag agcagcgaca agagcgtgtg cctgttcacc      60
gacttcgaca gccagaccaa cgtgtcccag agcaaggaca gcgacgtgta catcaccgat     120
aagtgcgtgc tggacatgcg gagcatggac ttcaagagca cagcgccgt ggcctggtcc      180
aacaagagcg atttcgcctg cgccaacgcc ttcaacaaca gcattatccc cgaggacaca     240
ttcttcccaa gccccgagag cagctgcgac gtgaagctgg tggaaaagag cttcgagaca     300
gacaccaacc tgaacttcca gaacctgagc gtgatcggct tcagaatcct gctgctgaag     360
gtggccggct caacctgct gatgaccctg agactgtggt cctccgct                   408
```

<210> SEQ ID NO 7
<211> LENGTH: 174
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
ggcctaactg gccggcacct gagccagatg acggtggaaa aattgcatca tacagaaggc      60
ttggaggaaa aactgtttca atcactacgc tcggaggaaa atttgtatca ttgagatggc     120
ctcggcggcc agaagccggc tgtagagggt atataatgga agctcgaatt ccag           174
```

<210> SEQ ID NO 8
<211> LENGTH: 104
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8

```
ggcacctgag ccagatgacg gtggaaaaat tgcatcatac agaaggcttg gaggaaaaac      60
tgtttcaatc actacgctcg gaggaaaatt tgtatcattg agat                      104
```

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9

```
tagagggtat ataatggaag ctcgaattcc ag                                    32
```

<210> SEQ ID NO 10
<211> LENGTH: 1587
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10

```
ggcctaactg gccggcacct gagccagatg acggtggaaa aattgcatca tacagaaggc      60
ttggaggaaa aactgtttca atcactacgc tcggaggaaa atttgtatca ttgagatggc     120
ctcggcggcc agaagccggc tgtagagggt atataatgga agctcgaatt ccagcctggc     180
cttccggtac tgttggtaga aggcctggca gagcggcacc gtgggaaagg ccaccatgtt     240
ggactttcaa gtgcagatct tcagcttcct gctgatctcc gccagcgtga tcatgagcag     300
aggccaggtg cagctggtgg aatctggacc tggcgtggtg cagccaggca gaagcctgag     360
aatcagctgt gccgtgtccg gcttcagcgt gaccaactac ggcgtgcact gggtgcgcca     420
gcctccaggc aaaggactgg aatggctggg cgtgatctgg gctggcggca tcaccaacta     480
caacagcgcc ttcatgagcc ggctgaccat cagcaaggac aacagcaaga caccgtgta      540 cctgcagatg aacagcctgc gggccgagga caccgccatg tactactgtg ctagcagagg     600
cggccactac ggctacgccc tggattattg gggccagggc acactcgtga ccgtgtctag     660
cggaggcgga ggatctggcg gcggaggaag tggcggaggg ggatctgaga tcgtgatgac     720
ccagacccct gccacccgtt ctgtgtctgc cggcgagaga gtgaccatta cctgcaaggc     780
cagccagagc gtgtccaacg acgtgacctg gtatcagcag aagcccggcc aggcccccag     840
actgctgatc tacagcgcca gcaaccggta cagcggagtg cccgccagat tttccggcag     900
cggctacggc accagttca ccttcaccat cagcagcgtg cagagcgagg acttcgccgt      960
gtacttctgt cagcaagact acagcagctt cggccagggc accaagctgg aaatcaagag    1020
atccggcgga ggctccggct accctacga cgtgcccgac tatgcattgg acctgcggca    1080
gggcatgttc gcccagctgg tgctcagaa cgtgctgctg atcgacggcc ccctgagctg    1140
gtactctgat cctggactgg ctggcgtgtc cctgaccggc ggactgagct acaaagagga    1200
cacaaaagaa ctggtggtgg ccaaggccgg cgtgtactac gtgttctttc agctggaact    1260
gcggagagtg gtgccggcg agggatctgg atctgtgtct ctggcctgc atctgcagcc    1320 cctgagatct gctgctggcg cagctgctct ggctctgacc gtggatctgc ctcctgccag    1380
```

```
cagcgaggcc agaaacagcg cattcgggtt tcaaggcagg ctgctgcacc tgagcgccgg    1440
acagagactg ggagtgcatc tgcacacaga ggcagagcc aggcacgcct ggcagctgac     1500
acagggcgct acagtgctgg gcctgttcag agtgaccccc gagattcctg ccggcctgcc    1560
tagccctaga agcgaccact aagttgg                                        1587
```

<210> SEQ ID NO 11
<211> LENGTH: 448
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 11

```
Met Leu Asp Phe Gln Val Gln Ile Phe Ser Phe Leu Leu Ile Ser Ala
1               5                   10                  15

Ser Val Ile Met Ser Arg Gly Gln Val Gln Leu Val Glu Ser Gly Pro
            20                  25                  30

Gly Val Val Gln Pro Gly Arg Ser Leu Arg Ile Ser Cys Ala Val Ser
        35                  40                  45

Gly Phe Ser Val Thr Asn Tyr Gly Val His Trp Val Arg Gln Pro Pro
    50                  55                  60

Gly Lys Gly Leu Glu Trp Leu Gly Val Ile Trp Ala Gly Gly Ile Thr
65                  70                  75                  80

Asn Tyr Asn Ser Ala Phe Met Ser Arg Leu Thr Ile Ser Lys Asp Asn
                85                  90                  95

Ser Lys Asn Thr Val Tyr Leu Gln Met Asn Ser Leu Arg Ala Glu Asp
            100                 105                 110

Thr Ala Met Tyr Tyr Cys Ala Ser Arg Gly Gly His Tyr Gly Tyr Ala
        115                 120                 125

Leu Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Glu Ile Val
145                 150                 155                 160

Met Thr Gln Thr Pro Ala Thr Leu Ser Val Ser Ala Gly Glu Arg Val
                165                 170                 175

Thr Ile Thr Cys Lys Ala Ser Gln Ser Val Ser Asn Asp Val Thr Trp
            180                 185                 190

Tyr Gln Gln Lys Pro Gly Gln Ala Pro Arg Leu Leu Ile Tyr Ser Ala
        195                 200                 205

Ser Asn Arg Tyr Ser Gly Val Pro Ala Arg Phe Ser Gly Ser Gly Tyr
    210                 215                 220

Gly Thr Glu Phe Thr Phe Thr Ile Ser Ser Val Gln Ser Glu Asp Phe
225                 230                 235                 240

Ala Val Tyr Phe Cys Gln Gln Asp Tyr Ser Ser Phe Gly Gln Gly Thr
                245                 250                 255

Lys Leu Glu Ile Lys Arg Ser Gly Gly Gly Ser Gly Tyr Pro Tyr Asp
            260                 265                 270

Val Pro Asp Tyr Ala Leu Asp Leu Arg Gln Gly Met Phe Ala Gln Leu
        275                 280                 285

Val Ala Gln Asn Val Leu Leu Ile Asp Gly Pro Leu Ser Trp Tyr Ser
    290                 295                 300

Asp Pro Gly Leu Ala Gly Val Ser Leu Thr Gly Gly Leu Ser Tyr Lys
305                 310                 315                 320
```

Glu Asp Thr Lys Glu Leu Val Val Ala Lys Ala Gly Val Tyr Tyr Val
            325                 330                 335

Phe Phe Gln Leu Glu Leu Arg Arg Val Val Ala Gly Glu Gly Ser Gly
            340                 345                 350

Ser Val Ser Leu Ala Leu His Leu Gln Pro Leu Arg Ser Ala Ala Gly
            355                 360                 365

Ala Ala Ala Leu Ala Leu Thr Val Asp Leu Pro Pro Ala Ser Ser Glu
            370                 375                 380

Ala Arg Asn Ser Ala Phe Gly Phe Gln Gly Arg Leu Leu His Leu Ser
385                 390                 395                 400

Ala Gly Gln Arg Leu Gly Val His Leu His Thr Glu Ala Arg Ala Arg
            405                 410                 415

His Ala Trp Gln Leu Thr Gln Gly Ala Thr Val Leu Gly Leu Phe Arg
            420                 425                 430

Val Thr Pro Glu Ile Pro Ala Gly Leu Pro Ser Pro Arg Ser Asp His
            435                 440                 445

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Pro Tyr Asp Val Pro Asp Tyr Ala
1               5

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tacccctacg acgtgcccga ctatgca                                          27

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Gly Gly Ser Gly
1               5

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tccggcggag gctccggc                                                    18

<210> SEQ ID NO 16
<211> LENGTH: 262
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Leu Asp Phe Gln Val Gln Ile Phe Ser Phe Leu Leu Ile Ser Ala
1               5                   10                  15

Ser Val Ile Met Ser Arg Gly Gln Val Gln Leu Val Glu Ser Gly Pro
            20                  25                  30

Gly Val Val Gln Pro Gly Arg Ser Leu Arg Ile Ser Cys Ala Val Ser
        35                  40                  45

Gly Phe Ser Val Thr Asn Tyr Gly Val His Trp Val Arg Gln Pro Pro
    50                  55                  60

Gly Lys Gly Leu Glu Trp Leu Gly Val Ile Trp Ala Gly Gly Ile Thr
65                  70                  75                  80

Asn Tyr Asn Ser Ala Phe Met Ser Arg Leu Thr Ile Ser Lys Asp Asn
                85                  90                  95

Ser Lys Asn Thr Val Tyr Leu Gln Met Asn Ser Leu Arg Ala Glu Asp
            100                 105                 110

Thr Ala Met Tyr Tyr Cys Ala Ser Arg Gly Gly His Tyr Gly Tyr Ala
        115                 120                 125

Leu Asp Tyr Trp Gly Gln Gly Thr Leu Val Thr Val Ser Ser Gly Gly
    130                 135                 140

Gly Gly Ser Gly Gly Gly Ser Gly Gly Gly Ser Glu Ile Val
145                 150                 155                 160

Met Thr Gln Thr Pro Ala Thr Leu Ser Val Ser Ala Gly Glu Arg Val
                165                 170                 175

Thr Ile Thr Cys Lys Ala Ser Gln Ser Val Ser Asn Asp Val Thr Trp
            180                 185                 190

Tyr Gln Gln Lys Pro Gly Gln Ala Pro Arg Leu Leu Ile Tyr Ser Ala
        195                 200                 205

Ser Asn Arg Tyr Ser Gly Val Pro Ala Arg Phe Ser Gly Ser Gly Tyr
    210                 215                 220

Gly Thr Glu Phe Thr Phe Thr Ile Ser Ser Val Gln Ser Glu Asp Phe
225                 230                 235                 240

Ala Val Tyr Phe Cys Gln Gln Asp Tyr Ser Ser Phe Gly Gln Gly Thr
                245                 250                 255

Lys Leu Glu Ile Lys Arg
            260
```

<210> SEQ ID NO 17
<211> LENGTH: 786
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
atgttggact tcaagtgca gatcttcagc ttcctgctga tctccgccag cgtgatcatg      60
agcagaggcc aggtgcagct ggtggaatct ggacctggcg tggtgcagcc aggcagaagc    120
ctgagaatca gctgtgccgt gtccggcttc agcgtgacca actacggcgt gcactgggtg    180
```

-continued

```
cgccagcctc caggcaaagg actggaatgg ctgggcgtga tctgggctgg cggcatcacc      240
aactacaaca gcgccttcat gagccggctg accatcagca aggacaacag caagaacacc      300
gtgtacctgc agatgaacag cctgcggggcc gaggacaccg ccatgtacta ctgtgctagc     360
agaggcggcc actacggcta cgccctggat tattggggcc agggcacact cgtgaccgtg      420
tctagcggag gcggaggatc tggcggcgga ggaagtggcg gaggggggatc tgagatcgtg    480 atgacccaga cccctgccac cctgtctgtg tctgccggcg agagtgac cattacctgc       540 aaggccagcc agagcgtgtc caacgacgtg acctggtatc agcagaagcc cggccaggcc     600
cccagactgc tgatctacag cgccagcaac cggtacagcg agtgcccgc cagatttttcc    660 ggcagcggct acggcaccga gttcaccttc accatcagca gcgtgcagag cgaggacttc     720
gccgtgtact ctgtcagca agactacagc agcttcggcc agggcaccaa gctggaaatc      780
aagaga                                                                 786
```

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 19
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
ggatccggcg ccaccaactt cagcctgctg aaacaggccg gggatgtgga agagaaccct      60
ggccct                                                                 66
```

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 21
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
tgatcggctt cagaatcctg ctgctgaagg tggccggatt caacctgctg atgaccctgc      60
ggctgtggtc ctccgcgggg agcggcgagg gaagaggatc tctgctaaca tgcggtgacg     120
ttgaggagaa tcccggaccg                                                 140
```

<210> SEQ ID NO 22
<211> LENGTH: 331
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 22

```
Pro Pro Arg Leu Leu Phe Phe Leu Leu Phe Leu Thr Pro Met Glu Val
1               5                   10                  15

Arg Pro Glu Glu Pro Leu Val Val Lys Val Glu Glu Gly Asp Asn Ala
            20                  25                  30

Val Leu Gln Cys Leu Lys Gly Thr Ser Asp Gly Pro Thr Gln Gln Leu
        35                  40                  45

Thr Trp Ser Arg Glu Ser Pro Leu Lys Pro Phe Leu Lys Leu Ser Leu
    50                  55                  60

Gly Leu Pro Gly Leu Gly Ile His Met Arg Pro Leu Ala Ile Trp Leu
65                  70                  75                  80

Phe Ile Phe Asn Val Ser Gln Gln Met Gly Gly Phe Tyr Leu Cys Gln
                85                  90                  95

Pro Gly Pro Pro Ser Glu Lys Ala Trp Gln Pro Gly Trp Thr Val Asn
            100                 105                 110

Val Glu Gly Ser Gly Glu Leu Phe Arg Trp Asn Val Ser Asp Leu Gly
        115                 120                 125

Gly Leu Gly Cys Gly Leu Lys Asn Arg Ser Ser Glu Gly Pro Ser Ser
    130                 135                 140

Pro Ser Gly Lys Leu Met Ser Pro Lys Leu Tyr Val Trp Ala Lys Asp
145                 150                 155                 160

Arg Pro Glu Ile Trp Glu Gly Glu Pro Pro Cys Leu Pro Arg Asp
                165                 170                 175

Ser Leu Asn Gln Ser Leu Ser Gln Asp Leu Thr Met Ala Pro Gly Ser
            180                 185                 190

Thr Leu Trp Leu Ser Cys Gly Val Pro Pro Asp Ser Val Ser Arg Gly
        195                 200                 205

Pro Leu Ser Trp Thr His Val His Pro Lys Gly Pro Lys Ser Leu Leu
    210                 215                 220

Ser Leu Glu Leu Lys Asp Asp Arg Pro Ala Arg Asp Met Trp Val Met
225                 230                 235                 240

Glu Thr Gly Leu Leu Leu Pro Arg Ala Thr Ala Gln Asp Ala Gly Lys
                245                 250                 255

Tyr Tyr Cys His Arg Gly Asn Leu Thr Met Ser Phe His Leu Glu Ile
            260                 265                 270

Thr Ala Arg Pro Val Leu Trp His Trp Leu Leu Arg Thr Gly Gly Trp
        275                 280                 285

Lys Val Ser Ala Val Thr Leu Ala Tyr Leu Ile Phe Cys Leu Cys Ser
    290                 295                 300

Leu Val Gly Ile Leu His Leu Gln Arg Ala Leu Val Leu Arg Arg Lys
305                 310                 315                 320
```

Arg Lys Arg Met Thr Asp Pro Thr Arg Arg Phe
            325                 330

<210> SEQ ID NO 23
<211> LENGTH: 996
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

| | | | | | |
|---|---|---|---|---|---|
| cccctcggc | tgctgttctt | cctgctgttc | ctgacccta | tggaagtgcg | gcccgaggaa | 60 |
| cccctggtcg | tgaaagtgga | agagggcgac | aacgccgtgc | tgcagtgtct | gaagggcacc | 120 |
| tccgatggcc | ctacccagca | gctgacatgg | tccagagaga | gcccctgaa | gcccttcctg | 180 |
| aagctgagcc | tgggactgcc | tggcctgggc | atccatatga | ggccactggc | catctggctg | 240 |
| ttcatcttca | cgtgtccca | gcagatgggc | ggcttctacc | tgtgtcagcc | tggccccca | 300 |
| agcgagaaag | cctggcagcc | tggctggacc | gtgaacgtgg | aaggatctgg | cgagctgttc | 360 |
| cggtggaacg | tgtccgatct | gggcggactg | gctgcggcc | tgaagaacag | aagcagcgag | 420 |
| ggccctagca | gccccagcgg | caaactgatg | agccccaagc | tgtacgtgtg | gccaaggac | 480 |
| cggcccgaga | tttgggaagg | cgagcctcct | tgcctgcccc | ccagagacag | cctgaatcag | 540 |
| agcctgagcc | aggacctgac | aatggcccct | ggcagcacac | tgtggctgag | ctgtggcgtg | 600 |
| ccacccgact | ctgtgtccag | aggccctctg | agctggaccc | acgtgcaccc | taagggcct | 660 |
| aagagcctgc | tgtccctgga | actgaaggac | gacagacccg | ccagagatat | gtgggtcatg | 720 |
| gaaaccggcc | tgctgctgcc | tagagccacc | gctcaggatg | ccggaaagta | ctactgccac | 780 |
| cggggcaacc | tgaccatgag | cttccacctg | gaaatcaccg | ccagaccgt | gctgtggcac | 840 |
| tggctgctga | gaaccggcgg | atggaaagtg | tccgccgtga | ccctggccta | cctgatcttc | 900 |
| tgcctgtgct | ccctcgtggg | catcctgcat | ctgcagcggg | ctctggtgct | gcggcggaag | 960 |
| agaaagagaa | tgaccgaccc | cacccgcaga | ttctaa | | | 996 |

<210> SEQ ID NO 24
<211> LENGTH: 2916
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

| | | | | | |
|---|---|---|---|---|---|
| atggacttcc | aggttcagat | cttctccttt | ctcctgatat | ccgcatctgt | gattatgtct | 60 |
| cgggggtcagg | tgcagctggt | tgaatctgga | cctggtgtgg | tacagcctgg | acggagcctg | 120 |
| cgaatctcat | gcgctgtctc | cggtttctct | gtaaccaact | atggagtgca | ctgggtgcgg | 180 |
| cagcctccag | gcaagggcct | ggaatggctc | ggagttatct | gggctggcgg | aattacaaat | 240 |
| tataattccg | cttttatgag | caggttgaca | attagtaaag | acaattctaa | gaacaccgtt | 300 |
| tatcttcaga | tgaatagctt | gagagctgag | gataccgcca | tgtactattg | tgcatcaaga | 360 |
| ggcgggcact | acggatacgc | gctcgactac | tggggacagg | ggacacttgt | gactgtcagt | 420 |
| tctggaggcg | gtgggagcga | ctataaagac | gacgatgaca | agggtggcgg | aggaagcgag | 480 |
| atcgtaatga | ctcagactcc | cgctacactg | agtgttagtg | ccggagagcg | cgttacaatc | 540 |
| acttgcaagg | catcacaatc | tgtttccaac | gacgtcactt | ggtaccagca | gaagcctggg | 600 |

```
caggctccta gattgctgat ttactccgct agcaatcgct actctggggt ccctgctcgc    660
tttagtggaa gtggctatgg cactgagttt accttcacca tcagcagcgt ccagtcagaa    720
gactttgccg tgtacttctg ccaacaggac tatagctcat ttggtcaggg aaccaagctt    780
gagatcaaac gcgtcgacct gaacaaggtg ttcccacccg aggtcgctgt gtttgagcca    840
tcagaagcag agatatccca cacccaaaag gccacactgg tgtgcctggc acaggcttc     900 ttccccgacc acgtggagct gagctggtgg gtgaatggga aggaggtgca cagtggggtc    960
tgcacggacc cgcagcccct caaggagcag cccgccctca tgactccag atactgcctg     1020 agcagccgct gagggtctc ggccaccttc tggcagaacc cccgcaacca cttccgctgt      1080
caagtccagt tctacgggct ctcggagaat gacgagtgga cccaggatag ggccaaaccc    1140
gtcacccaga tcgtcagcgc cgaggcctgg ggtagagcag actgtggctt tacctcggtg    1200
tcctaccagc aagggtcct gtctgccacc atcctctatg atcctgct agggaaggcc       1260 accctgtatg ctgtgctggt cagcgcccct gtgttgatgg ctatggtcaa gagaaaggga    1320
tccggcgcca ccaacttcag cctgctgaaa caggccgggg atgtggaaga aaccctggc     1380 ccttcgaaaa gcctgcgggt gctgctcgtg atcctgtggc tgcagctgag ctgggtgtgg    1440
agcgcatgcc ctgccgtgta ccagctgaga gacagcaaga gcagcgacaa gagcgtgtgc    1500
ctgttcaccg acttcgacag ccagaccaac gtgtcccaga gcaaggactc cgatgtgtac    1560
atcaccgata agtgcgtgct ggacatgcgg agcatggact tcaagagcaa cagcgccgtg    1620
gcctggtcca acaagagcga tttcgcctgc gccaacgcct tcaacaacag cattatcccc    1680
gaggacacat tcttcccaag ccccgagagc agctgtgatg tgaagctggt ggaaaagagc    1740
ttcgagacag acaccaacct gaacttccag aacctgagcg tgatcggctt cagaatcctg    1800
ctgctgaagg tggccggatt caacctgctg atgaccctgc ggctgtggtc ctccgcgggg    1860
agcggcgagg aaagaggatc tctgctaaca tgcggtgacg ttgaggagaa tcccggaccg    1920 cccctcggc tgctgttctt cctgctgttc ctgaccccta tggaagtgcg gcccgaggaa     1980
cccctggtcg tgaaagtgga agagggcgac aacgccgtgc tgcagtgtct gaagggcacc    2040
tccgatggcc ctacccagca gctgacatgg tccagagaga ccccctgaa gcccttcctg      2100 aagctgagcc tgggactgcc tggcctgggc atccatatga ggccactggc catctggctg    2160
ttcatcttca acgtgtccca gcagatgggc ggcttctacc tgtgtcagcc tggcccccca    2220
agcgagaaag cctggcagcc tggctggacc gtgaacgtgg aaggatctgg cgagctgttc    2280
cggtggaacg tgtccgatct gggcggactg ggctgcggcc tgaagaacag aagcagcgag    2340
ggccctagca gccccagcgg caaactgatg agccccaagc tgtacgtgtg gccaaggac     2400 cggcccgaga tttgggaagg cgagcctcct tgcctgcccc ccagagacag cctgaatcag    2460
agcctgagcc aggacctgac aatggcccct ggcagcacac tgtggctgag ctgtggcgtg    2520
ccacccgact ctgtgtccag aggccctctg agctggaccc acgtgcaccc taagggccct    2580
aagagcctgc tgtccctgga actgaaggac acagacccg ccagagatat gtgggtcatg     2640
gaaaccggcc tgctgctgcc tagagccacc gctcaggatg ccggaaagta ctactgccac    2700
cggggcaacc tgaccatgag cttccacctg gaaatcaccg ccagacccgt gctgtggcac    2760 tgctgctga gaaccggcgg atggaaagtg tccgccgtga ccctggccta cctgatcttc    2820
tgcctgtgct ccctcgtggg catcctgcat ctgcagcggg ctctggtgct gcggcggaag    2880
agaaagagaa tgaccgaccc cacccgcaga ttctaa                              2916
```

<210> SEQ ID NO 25
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Leu Asp Phe Gln Val Gln Ile Phe Ser Phe Leu Leu Ile Ser Ala
1               5                   10                  15

Ser Val Ile Met Ser Arg Gly Gln Val Gln Leu Val Glu Ser Gly Pro
            20                  25                  30

Gly Val Val Gln Pro Gly Arg Ser Leu Arg Ile Ser Cys Ala Val Ser
        35                  40                  45

Gly Phe Ser Val Thr Asn Tyr Gly Val His Trp Val Arg Gln Pro Pro
    50                  55                  60

Gly Lys Gly Leu Glu Trp Leu Gly Val Ile Trp Ala Gly Gly Ile Thr
65                  70                  75                  80

Asn Tyr Asn Ser Ala Phe Met Ser Arg Leu Thr Ile Ser Lys Asp Asn
                85                  90                  95

Ser Lys Asn Thr Val Tyr Leu Gln Met Asn Ser Leu Arg Ala Glu Asp
            100                 105                 110

Thr Ala Met Tyr Tyr Cys Ala Ser Arg Gly His Tyr Gly Tyr Ala
        115                 120                 125

Leu Asp Tyr Trp Gly Gln Gly Thr Leu Val Thr Val Ser Ser Gly Gly
    130                 135                 140

Gly Gly Ser Gly Gly Gly Ser Gly Gly Gly Ser Glu Ile Val
145                 150                 155                 160

Met Thr Gln Thr Pro Ala Thr Leu Ser Val Ser Ala Gly Glu Arg Val
                165                 170                 175

Thr Ile Thr Cys Lys Ala Ser Gln Ser Val Ser Asn Asp Val Thr Trp
            180                 185                 190

Tyr Gln Gln Lys Pro Gly Gln Ala Pro Arg Leu Leu Ile Tyr Ser Ala
        195                 200                 205

Ser Asn Arg Tyr Ser Gly Val Pro Ala Arg Phe Ser Gly Ser Gly Tyr
    210                 215                 220

Gly Thr Glu Phe Thr Phe Thr Ile Ser Ser Val Gln Ser Glu Asp Phe
225                 230                 235                 240

Ala Val Tyr Phe Cys Gln Gln Asp Tyr Ser Ser Phe Gly Gln Gly Thr
                245                 250                 255

Lys Leu Glu Ile Lys Arg Ser Gly Gly Gly Ser Gly Tyr Pro Tyr Asp
            260                 265                 270

Val Pro Asp Tyr Ala Leu Asp Leu Arg Gln Gly Met Phe Ala Gln Leu
        275                 280                 285

Val Ala Gln Asn Val Leu Leu Ile Asp Gly Pro Leu Ser Trp Tyr Ser
    290                 295                 300

Asp Pro Gly Leu Ala Gly Val Ser Leu Thr Gly Gly Leu Ser Tyr Lys
305                 310                 315                 320

Glu Asp Thr Lys Glu Leu Val Val Ala Lys Ala Gly Val Tyr Tyr Val
                325                 330                 335

Phe Phe Gln Leu Glu Leu Arg Arg Val Val Ala Gly Glu Gly Ser Gly
            340                 345                 350

Ser Val Ser Leu Ala Leu His Leu Gln Pro Leu Arg Ser Ala Ala Gly
        355                 360                 365
```

```
Ala Ala Ala Leu Ala Leu Thr Val Asp Leu Pro Pro Ala Ser Ser Glu
        370                 375                 380

Ala Arg Asn Ser Ala Phe Gly Phe Gln Gly Arg Leu Leu His Leu Ser
385                 390                 395                 400

Ala Gly Gln Arg Leu Gly Val His Leu His Thr Glu Ala Arg Ala Arg
                405                 410                 415

His Ala Trp Gln Leu Thr Gln Gly Ala Thr Val Leu Gly Leu Phe Arg
            420                 425                 430

Val Thr Pro Glu Ile Pro Ala Gly Leu Pro Ser Pro Arg Ser Asp His
        435                 440                 445

<210> SEQ ID NO 26
<211> LENGTH: 1582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ggcctaactg gccggcacct gagccagatg acggtggaaa aattgcatca tacagaaggc      60
ttggaggaaa aactgtttca atcactacgc tcggaggaaa atttgtatca ttgagatggc     120
ctcggcggcc agaagccggc tgtagagggt atataatgga agctcgaatt ccagcctggc     180
cttccggtac tgttggtaga aggcctggca gagcggcacc gtgggaaagg ccaccatgtt     240
ggactttcaa gtgcagatct tcagcttcct gctgatctcc gccagcgtga tcatgagcag     300
aggccaggtg cagctggtgg aatctggacc tggcgtggtg cagccaggca gaagcctgag     360
aatcagctgt gccgtgtccg gcttcagcgt gaccaactac ggcgtgcact gggtgcgcca     420
gcctccaggc aaaggactgg aatggctggg cgtgatctgg ctggcggca tcaccaacta     480 caacagcgcc ttcatgagcc ggctgaccat cagcaaggac aacagcaaga caccgtgta     540 cctgcagatg aacagcctgc gggccgagga caccgccatg tactactgtg ctagcagagg     600
cggccactac ggctacgccc tggattattg gggccagggc acactcgtga ccgtgtctag     660
cggaggcgga ggatctggcg gcggaggaag tggcggaggg ggatctgaga tcgtgatgac     720
ccagacccct gccaccctgt ctgtgtctgc cggcgagaga gtgaccatta cctgcaaggc     780
cagccagagc gtgtccaacg acgtgacctg gtatcagcag aagcccggcc aggcccccag     840
actgctgatc tacagcgcca gcaaccggta cagcggagtg cccgccagat tttccggcag     900
cggctacggc accgagttca ccttcaccat cagcagcgtg cagagcgagg acttcgccgt     960
gtacttctgt cagcaagact acagcagctt cggccagggc accaagctgg aaatcaagag    1020
atccggcgga ggctccggct accccctacga cgtgcccgac tatgcattgg acctgcggca    1080
gggcatgttc gcccagctgg tggctcagaa cgtgctgctg atcgacggcc ccctgagctg    1140
gtactctgat cctggactgg ctggcgtgtc cctgaccggc ggactgagct acaaagagga    1200
cacaaaagaa ctggtggtgg ccaaggccgg cgtgtactac gtgttctttc agctggaact    1260
gcggagagtg gtgccggcg agggatctgg atcgtgtct ctggccctgc atctgcagcc    1320
cctgagatct gctgctggcg cagctgctct ggctctgacc gtggatctgc ctcctgccag    1380
cagcgaggcc agaaacagcg cattcgggtt tcaaggcagg ctgctgcacc tgagcgccgg    1440
```

```
acagagactg ggagtgcatc tgcacacaga ggccagagcc aggcacgcct ggcagctgac    1500
acagggcgct acagtgctgg gcctgttcag agtgaccccc gagattcctg ccggcctgcc    1560
tagccctaga agcgaccact aa                                             1582
```

<210> SEQ ID NO 27
<211> LENGTH: 988
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gtcgacctga acaaggtgtt cccacccgag gtcgctgtgt ttgagccatc agaagcagag      60
atatcccaca cccaaaaggc cacactggtg tgcctggcca caggcttctt ccccgaccac     120
gtggagctga gctggtgggt gaatgggaag gaggtgcaca gtggggtctg cacggacccg     180
cagcccctca aggagcagcc cgccctcaat gactccagat actgcctgag cagccgcctg     240
agggtctcgg ccaccttctg gcagaacccc cgcaaccact tccgctgtca agtccagttc     300
tacgggctct cggagaatga cgagtggacc caggataggg ccaaacccgt cacccagatc     360
gtcagcgccg aggcctgggg tagagcagac tgtggctttta cctcggtgtc ctaccagcaa     420
ggggtcctgt ctgccaccat cctctatgag atcctgctag gaaggccac cctgtatgct     480 gtgctggtca gcgcccttgt gttgatggct atggtcaaga gaaagggatc cggcgccacc     540
aacttcagcc tgctgaaaca ggccggggat gtggaagaga accctggccc ttcgaaaagc     600
ctgcgggtgc tgctcgtgat cctgtggctg cagctgagct gggtgtggag cgcatgccct     660
gccgtgtacc agctgagaga cagcaagagc agcgacaaga gcgtgtgcct gttcaccgac     720
ttcgacagcc agaccaacgt gtcccagagc aaggactccg atgtgtacat caccgataag     780
tgcgtgctgg acatgcggag catggacttc aagagcaaca gcgccgtggc ctggtccaac     840
aagagcgatt tcgcctgcgc caacgccttc aacaacagca ttatccccga ggacacattc     900
ttcccaagcc ccgagagcag ctgtgatgtg aagctggtgg aaaagagctt cgagacagac     960
accaacctga acttccagaa cctgagcg                                        988
```

<210> SEQ ID NO 28
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Leu Val Arg Arg Gly Ala Arg Ala Gly Pro Arg Met Pro Arg Gly Trp
1               5                   10                  15

Thr Ala Leu Cys Leu Leu Ser Leu Leu Pro Ser Gly Phe Met Ser Leu
            20                  25                  30

Asp Asn Asn Gly Thr Ala Thr Pro Glu Leu Pro Thr Gln Gly Thr Phe
        35                  40                  45

Ser Asn Val Ser Thr Asn Val Ser Tyr Gln Glu Thr Thr Thr Pro Ser
    50                  55                  60

Thr Leu Gly Ser Thr Ser Leu His Pro Val Ser Gln His Gly Asn Glu
65                  70                  75                  80
```

Ala Thr Thr Asn Ile Thr Glu Thr Thr Val Lys Phe Thr Ser Thr Ser
             85                  90                  95

Val Ile Thr Ser Val Tyr Gly Asn Thr Asn Ser Ser Val Gln Ser Gln
            100                 105                 110

Thr Ser Val Ile Ser Thr Val Phe Thr Thr Pro Ala Asn Val Ser Thr
            115                 120                 125

Pro Glu Thr Thr Leu Lys Pro Ser Leu Ser Pro Gly Asn Val Ser Asp
130                 135                 140

Leu Ser Thr Thr Ser Thr Ser Leu Ala Thr Ser Pro Thr Lys Pro Tyr
145                 150                 155                 160

Thr Ser Ser Ser Pro Ile Leu Ser Asp Ile Lys Ala Glu Ile Lys Cys
                165                 170                 175

Ser Gly Ile Arg Glu Val Lys Leu Thr Gln Gly Ile Cys Leu Glu Gln
            180                 185                 190

Asn Lys Thr Ser Ser Cys Ala Glu Phe Lys Lys Asp Arg Gly Glu Gly
            195                 200                 205

Leu Ala Arg Val Leu Cys Gly Glu Gln Ala Asp Ala Asp Ala Gly
        210                 215                 220

Ala Gln Val Cys Ser Leu Leu Ala Gln Ser Glu Val Arg Pro Gln
225                 230                 235                 240

Cys Leu Leu Leu Val Leu Ala Asn Arg Thr Glu Ile Ser Ser Lys Leu
                245                 250                 255

Gln Leu Met Lys Lys His Gln Ser Asp Leu Lys Lys Leu Gly Ile Leu
            260                 265                 270

Asp Phe Thr Glu Gln Asp Val Ala Ser His Gln Ser Tyr Ser Gln Lys
            275                 280                 285

Thr Leu Ile Ala Leu Val Thr Ser Gly Ala Leu Leu Ala Val Leu Gly
            290                 295                 300

Ile Thr Gly Tyr Phe Leu Met Asn Arg Arg Phe
305                 310                 315

<210> SEQ ID NO 29
<211> LENGTH: 948
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
ctcgttagaa gaggcgctag agctggcccc agaatgccta gaggatggac agctctgtgc      60
ctgctgagcc tgctgcctag cggctttatg agcctggaca caacggcac cgccacacct     120 gaactgccta cacagggcac cttcagcaat gtgtctacca acgtgtccta ccaagagaca    180
accacaccta gcacactggg cagcacatct ctgcaccctg tgtctcagca cggcaatgag   240
gccaccacca acatcaccga dcaaccgtg aagttcacct ctacctccgt gattaccagc     300
gtgtacggca acaccaacag cagcgtgcag agccagacaa gcgtgatcag caccgtgttc    360 acaaccctg ccaatgtgtc cacaccagaa accacactga gcccagcct gtctcctgga    420 aacgtgtccg atctgagcac cacctctaca agcctggcca cctctcctac aaagccctac     480
acaagcagca gccccatcct gagcgatatc aaggccgaga tcaagtgcag cggcatccgg    540
gaagtgaagc tgacccaggg catctgcctg gaacagaaca agaccagcag ctgcgccgag    600
ttcaagaagg acagaggcga aggactggcc agagtgctgt gtggcgaaga acaggccgat    660

```
gctgatgctg gcgctcaagt gtgctctctg ctgctggctc agtctgaagt gcggcctcag    720
tgtctgttgc tggtgctggc caacagaacc gagatcagca gcaaactgca gctgatgaag    780
aagcaccaga gcgacctgaa gaagctgggc atcctggact tcaccgagca ggatgtggcc    840
tctcaccaga gctacagcca gaaaaccctg atcgccctgg tcacatctgg cgctctgctg    900
gctgtgctgg gaatcaccgg ctactttctg atgaatcgga gattctaa                948
```

```
<210> SEQ ID NO 30
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30
```

| | | | | | | | | | | | | | | |
|---|---|---|---|---|---|---|---|---|---|---|---|---|---|---|
| Met | Val | Leu | Leu | Val | Thr | Ser | Leu | Leu | Leu | Cys | Glu | Leu | Pro | His | Pro |
| 1 | | | | 5 | | | | | 10 | | | | | 15 | |

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Gly Gly Gly Gly Ser Asp Tyr Lys Asp Asp Asp Lys Gly Gly Gly
    130                 135                 140

Gly Ser Glu Val Lys Leu Gln Glu Ser Gly Pro Gly Leu Val Ala Pro
145                 150                 155                 160

Ser Gln Ser Leu Ser Val Thr Cys Thr Val Ser Gly Val Ser Leu Pro
                165                 170                 175

Asp Tyr Gly Val Ser Trp Ile Arg Gln Pro Pro Arg Lys Gly Leu Glu
            180                 185                 190

Trp Leu Gly Val Ile Trp Gly Ser Glu Thr Thr Tyr Tyr Asn Ser Ala
        195                 200                 205

Leu Lys Ser Arg Leu Thr Ile Ile Lys Asp Asn Ser Lys Ser Gln Val
    210                 215                 220

Phe Leu Lys Met Asn Ser Leu Gln Thr Asp Asp Thr Ala Ile Tyr Tyr
225                 230                 235                 240

Cys Ala Lys His Tyr Tyr Tyr Gly Gly Ser Tyr Ala Met Asp Tyr Trp
                245                 250                 255

Gly Gln Gly Thr Ser Val Thr Val Ser
            260                 265

```
<210> SEQ ID NO 31
<211> LENGTH: 795
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 31

```
atggttctgc tcgtgacctc tctgctgctg tgcgagctgc cccaccctgc ctttctgctg      60
atccccgaca tccagatgac ccagaccacc agcagcctga gcgccagcct gggcgataga     120
gtgaccatca gctgcagagc cagccaggac atcagcaagt acctgaactg gtatcagcag     180
aaacccgacg gcaccgtgaa gctgctgatc taccacacca gcagactgca cagcggcgtg     240
cccagcagat ttctggcag cggctccggc accgactaca gcctgaccat ctccaacctg      300
gaacaggaag atattgctac ctacttctgt cagcaaggca cacccctgcc ctacaccttc     360
ggcggaggca ccaagctgga aatcggaggc ggcggaagcg actacaagga cgacgacgat     420
aagggcggag ggggcagcga agtgaaactg caggaatctg gccctggcct ggtggcccca     480
agccagtctc tgagcgtgac ctgtaccgtg tccggcgtgt ccctgcctga ctatggcgtg     540
tcctggatca gacagccccc cagaaagggc ctggaatggc tgggagtgat ctggggctcc     600
gagacaacct actacaacag cgccctgaag tcccggctga ccatcatcaa ggacaactcc     660
aagagccagg tgttcctgaa gatgaacagc ctgcagaccg acgacaccgc catctactac     720
tgcgccaagc actactacta cggcggcagc tacgctatgg actactgggg ccagggaacc     780
agcgtgaccg tgtct                                                      795
```

<210> SEQ ID NO 32
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu His Ser Thr Phe Leu Ser Gly Leu Val Leu Ala Thr Leu Leu Ser
1               5                   10                  15

Gln Val Ser Pro Phe Lys Ile Pro Ile Glu Glu Leu Glu Asp Arg Val
            20                  25                  30

Phe Val Asn Cys Asn Thr Ser Ile Thr Trp Val Glu Gly Thr Val Gly
        35                  40                  45

Thr Leu Leu Ser Asp Ile Thr Arg Leu Asp Leu Gly Lys Arg Ile Leu
    50                  55                  60

Asp Pro Arg Gly Ile Tyr Arg Cys Asn Gly Thr Asp Ile Tyr Lys Asp
65                  70                  75                  80

Lys Glu Ser Thr Val Gln Val His Tyr Arg Met Cys Gln Ser Cys Val
                85                  90                  95

Glu Leu Asp Pro Ala Thr Val Ala Gly Ile Ile Val Thr Asp Val Ile
            100                 105                 110

Ala Thr Leu Leu Leu Ala Leu Gly Val Phe Cys Phe Ala Gly His Glu
        115                 120                 125

Thr Gly Arg Leu Ser Gly Ala Ala Asp Thr Gln Ala Leu Leu Arg Asn
    130                 135                 140

Asp Gln Val Tyr Gln Pro Leu Arg Asp Arg Asp Ala Gln Tyr Ser
145                 150                 155                 160

His Leu Gly Gly Asn Trp Ala Arg Asn Lys Ser Gly Gly Gly Ser Lys
                165                 170                 175

Arg Gly Arg Lys Lys Leu Leu Tyr Ile Phe Lys Gln Pro Phe Met Arg
            180                 185                 190

Pro Val Gln Thr Thr Gln Glu Glu Asp Gly Cys Ser Cys Arg Phe Pro
        195                 200                 205

Glu Glu Glu Glu Gly Gly Cys Glu Leu
    210                 215

<210> SEQ ID NO 33
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gagcacagca cctttctgag cggactggtg ctggccaccc tgctgtctca ggtgtccccc      60
ttcaaaatcc ccatcgagga actgaagat cgggtgttcg tgaactgcaa caccagcatt     120
acctgggtgg aaggcaccgt gggcacactg ctgagcgaca tcaccagact ggacctgggc    180
aagagaatcc tggaccccag aggcatctac cggtgcaacg gcaccgacat ctacaaggac    240
aaagaaagca ccgtgcaggt gcactaccgg atgtgccaga gctgcgtgga actgaccct     300 gccacagtgg ccggcatcat cgtgaccgat gtgatcgcca ctctgctgct ggccctgggc    360
gtgttctgtt tcgccggaca cgagacaggc agactgagcg agccgccga tacacaggcc     420 ctgctgagaa cgaccaggt gtaccagccc ctgcgggaca gagatgacgc ccagtattct     480
cacctgggcg gcaactgggc ccggaacaaa tctggcggcg aagcaagcg gggcagaaag     540 aagctgctgt acatcttcaa gcagcccttc atgcggcccg tgcagaccac ccaggaagag    600
gacggctgct cctgcagatt ccccgaggaa gaagaaggcg gctgcgagct g              651

<210> SEQ ID NO 34
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Val Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
            85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
            130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Gly
                165                 170                 175

Gly Asn Lys Glu Lys Lys Ala Val Ser Pro Leu Leu Leu Thr Thr Thr
            180                 185                 190

Asn Ser Ser Glu Gly Leu Ser Met Gly Asn Tyr Ile Gly Ser Lys Arg
        195                 200                 205

Gly Arg Lys Lys Leu Leu Tyr Ile Phe Lys Gln Pro Phe Met Arg Pro
210                 215                 220

Val Gln Thr Thr Gln Glu Glu Asp Gly Cys Ser Cys Arg Phe Pro Glu
225                 230                 235                 240

Glu Glu Glu Gly Gly Cys Glu Leu
                245

<210> SEQ ID NO 35
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gtcgacctga acaaggtgtt ccccccagag gtggccgtgt cgagccttc tgaggccgag      60 atcagccaca cccagaaagc taccctcgtg tgcctggcca ccggcttttt ccccgaccac    120
gtggaactgt cttggtgggt caacggcaaa gaggtgcact ccggcgtgtg caccgatccc    180
cagcctctga agaacagcc cgccctgaac gacagccggt actgcctgag cagcagactg    240
agagtgtccg ccaccttctg gcagaacccc cggaaccact tcagatgcca ggtgcagttc    300
tacggcctga gcgagaacga cgagtggacc caggacagag ccaagcccgt gacccagatc    360
gtgtctgccg aagcctgggg cagagccgac tgtggcttta ccagcgtgtc ctatcagcag    420
ggcgtgctga gcgccaccat cctgtacgag atcctgctgg gcaaggccac cctgtacgcc    480
gtgctggtgt ctgccctggt gctgatggct atggtcaagc ggaagggcgg caacaaagaa    540
aagaaagccg tgtccccct gctgctgacc accaccaata gcagcgaggg cctgagcatg    600
ggcaactaca tcggcagcaa gcgggggcaga aagaagctgc tgtacatctt caagcagccc    660
ttcatgcggc ccgtgcagac cacccaggaa gaggacggct gctcctgcag attccccgag    720
gaagaagaag gcggctgcga gctg                                            744

<210> SEQ ID NO 36
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Lys Ser Leu Arg Val Leu Leu Val Ile Leu Trp Leu Gln Leu Ser
1               5                   10                  15

Trp Val Trp Ser Ala Cys Pro Ala Val Tyr Gln Leu Arg Asp Ser Lys
                20                  25                  30

```
Ser Ser Asp Lys Ser Val Cys Leu Phe Thr Asp Phe Asp Ser Gln Thr
         35                  40                  45

Asn Val Ser Gln Ser Lys Asp Ser Asp Val Tyr Ile Thr Asp Lys Cys
 50                  55                  60

Val Leu Asp Met Arg Ser Met Asp Phe Lys Ser Asn Ser Ala Val Ala
 65                  70                  75                  80

Trp Ser Asn Lys Ser Asp Phe Ala Cys Ala Asn Ala Phe Asn Asn Ser
                 85                  90                  95

Ile Ile Pro Glu Asp Thr Phe Phe Pro Ser Pro Glu Ser Ser Cys Asp
                100                 105                 110

Val Lys Leu Val Glu Lys Ser Phe Glu Thr Asp Thr Asn Leu Asn Phe
            115                 120                 125

Gln Asn Leu Ser Val Ile Gly Phe Arg Ile Leu Leu Leu Lys Val Ala
        130                 135                 140

Gly Phe Asn Leu Leu Met Thr Leu Arg Leu Trp Ser Ser Ala Gly Gly
145                 150                 155                 160

Asn Lys Glu Lys Lys Ala Val Ser Pro Leu Leu Leu Thr Thr Thr Asn
                165                 170                 175

Ser Ser Glu Gly Leu Ser Met Gly Asn Tyr Ile Gly Ser Lys Arg Gly
                180                 185                 190

Arg Lys Lys Leu Leu Tyr Ile Phe Lys Gln Pro Phe Met Arg Pro Val
            195                 200                 205

Gln Thr Thr Gln Glu Glu Asp Gly Cys Ser Cys Arg Phe Pro Glu Glu
        210                 215                 220

Glu Glu Gly Gly Cys Glu Leu
225                 230

<210> SEQ ID NO 37
<211> LENGTH: 693
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
tcgaaaagcc tgcgggtgct gctcgtgatc ctgtggctgc agctgagctg ggtgtggagc      60
gcatgccctg ccgtgtacca gctgagagac agcaagagca gcgacaagag cgtgtgcctg     120
ttcaccgact cgacagcca gaccaacgtg tcccagagca aggacagcga cgtgtacatc     180
accgataagt gcgtgctgga catgcggagc atggacttca gagcaacag cgccgtggcc     240 tggtccaaca gagcgattt cgcctgcgcc aacgccttca caacagcat tatccccgag     300 gacacattct tcccaagccc cgagagcagc tgcgacgtga agctggtgga aaagagcttc     360
gagacagaca ccaacctgaa cttccagaac ctgagcgtga tcggcttcag aatcctgctg     420
ctgaaggtgg ccggcttcaa cctgctgatg accctgagac tgtggtcctc cgctggcggc     480
aacaaagaaa agaaagccgt gtcccctctg ctgctgacca ccaccaatag cagcgagggc     540
ctgagcatgg gcaactacat cggcagcaag cggggcagaa agaagctgct gtacatcttc     600
aagcagccct tcatgcggcc cgtgcagacc acccaggaag aggacggctg ctcctgccgg     660
ttccccgaag aggaagaagg gggctgcgaa ctg                                   693

<210> SEQ ID NO 38
<211> LENGTH: 353
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 38

Gly Asn Ser Cys Tyr Asn Ile Val Ala Thr Leu Leu Val Leu Asn
1               5                   10                  15

Thr Ser Tyr Pro Tyr Asp Val Pro Asp Tyr Ala Ala Cys Gly Cys Ala
            20                  25                  30

Ala Ala Pro Asp Val Lys Glu Leu Leu Ser Arg Leu Glu Glu Leu Glu
            35                  40                  45

Asn Leu Val Ser Ser Leu Arg Glu Gln Cys Thr Ser Gly Gly Gly
50                      55                  60

Ser Ile Ile Ser Phe Phe Leu Ala Leu Thr Ser Thr Ala Leu Leu Phe
65                  70                  75                  80

Leu Leu Phe Phe Leu Thr Leu Arg Phe Ser Val Val Lys Arg Gly Arg
                85                  90                  95

Lys Lys Leu Leu Tyr Ile Phe Lys Gln Pro Phe Met Arg Pro Val Gln
                100                 105                 110

Thr Thr Gln Glu Glu Asp Gly Cys Ser Cys Arg Phe Pro Glu Glu Glu
            115                 120                 125

Glu Gly Gly Cys Glu Leu Glu Gln Ile Ala Glu Phe Lys Glu Ala Phe
            130                 135                 140

Ser Leu Phe Asp Lys Asp Gly Asp Gly Thr Ile Thr Thr Lys Glu Leu
145                 150                 155                 160

Gly Thr Val Met Arg Ser Leu Gly Gln Asn Pro Thr Glu Ala Glu Leu
                165                 170                 175

Gln Asp Met Ile Asn Glu Val Asp Ala Asp Gly Asn Gly Thr Ile Asp
            180                 185                 190

Phe Pro Glu Phe Leu Thr Met Met Ala Arg Lys Met Lys Asp Thr Gly
        195                 200                 205

Gly Val Arg Leu Ile Pro Ser Trp Thr Thr Val Ile Leu Val Lys Ser
        210                 215                 220

Met Leu Arg Lys Arg Ser Phe Gly Asn Pro Phe Gly Gly Asp Ser Glu
225                 230                 235                 240

Glu Glu Ile Arg Glu Ala Phe Arg Val Phe Asp Lys Asp Gly Asn Gly
                245                 250                 255

Tyr Ile Ser Ala Ala Glu Leu Arg His Val Met Thr Asn Leu Gly Glu
            260                 265                 270

Lys Leu Thr Asp Glu Glu Val Asp Glu Met Ile Arg Glu Ala Asp Ile
        275                 280                 285

Asp Gly Asp Gly Gln Val Asn Tyr Glu Glu Phe Val Gln Met Met Thr
290                 295                 300

Ala Lys Ser Gly Gly Gly Ser Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu

<210> SEQ ID NO 39
<211> LENGTH: 1059
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

| | | | | | |
|---|---|---|---|---|---|
| gggaactctt | gctacaacat | cgttgcaact | cttctcttgg | tcctcaatac | tagttatcca | 60 |
| tacgacgtcc | cggactatgc | cgcttgtggc | tgcgccgccg | ccccgatgt | caaggaactg | 120 |
| ctcagcaggt | tggaagagct | tgaaaatctg | gtttcctccc | ttcgagaaca | gtgtactagt | 180 |
| ggcggtggcg | gatctataat | ctctttcttt | ctcgctctca | ctagcaccgc | gttgcttttt | 240 |
| cttttgtttt | tcttgacgtt | gaggttctca | gttgttaagc | gaggccggaa | aaaactgctt | 300 |
| tacattttca | aacaaccctt | tatgcgacca | gttcaaacga | cgcaggagga | ggatggttgt | 360 |
| tcctgtcggt | ttccagaaga | ggaggaaggg | ggctgtgagc | ttgagcagat | tgcggaattt | 420 |
| aaggaagcat | tcagtctgtt | tgacaaagat | ggcgacggca | caattacaac | gaaagaactt | 480 |
| ggcacagtaa | tgcggtcact | gggtcagaat | ccgacagagg | ccgaactcca | ggacatgata | 540 |
| aatgaagttg | acgctgacgg | taacggaacc | attgattttc | ctgaatttct | taccatgatg | 600 |
| gcccgaaaaa | tgaaagatac | cggtggtgtc | agacttatac | ccagttggac | gacggtaatt | 660 |
| cttgtaaaat | ctatgctgcg | gaagcgcagt | ttcggcaacc | catttggcgg | ggactctgag | 720 |
| gaagagatcc | gagaagcgtt | ccgagtgttc | gataaggacg | gaaacggcta | catttccgca | 780 |
| gctgaactgc | gacatgtgat | gaccaacctt | ggggaaaagt | tgactgatga | agaagttgac | 840 |
| gaaatgatcc | gggaggctga | tatagacggg | gatggacaag | taaactacga | ggagttcgtt | 900 |
| cagatgatga | ccgcaaagtc | aggggtggt | tctaaacgcg | ccgcaaaaa | attgctttat | 960 |
| atctttaaac | aaccccttcat | gaggcctgtc | cagactacac | aggaggaaga | cggctgtagt | 1020 |
| tgtagatttc | ctgaggaaga | agaaggaggg | tgcgaactc | | | 1059 |

<210> SEQ ID NO 40
<211> LENGTH: 988
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

| | | | | | |
|---|---|---|---|---|---|
| gtcgacctga | acaaggtgtt | cccacccgag | gtcgctgtgt | tgagccatc | agaagcagag | 60 |
| atatcccaca | cccaaaaggc | cacactggtg | tgcctggcca | caggcttctt | ccccgaccac | 120 |
| gtggagctga | gctggtgggt | gaatgggaag | gaggtgcaca | gtggggtctg | cacggacccg | 180 |
| cagcccctca | aggagcagcc | cgccctcaat | gactccagat | actgcctgag | cagccgcctg | 240 |
| agggtctcgg | ccaccttctg | gcagaacccc | cgcaaccact | tccgctgtca | agtccagttc | 300 |
| tacgggctct | cggagaatga | cgagtggacc | caggataggg | ccaaacccgt | cacccagatc | 360 |
| gtcagcgccg | aggcctgggg | tagagcagac | tgtggcttta | cctcggtgtc | ctaccagcaa | 420 |
| ggggtcctgt | ctgccaccat | cctctatgag | atcctgctag | ggaaggccac | cctgtatgct | 480 |
| gtgctggtca | gcgcccttgt | gttgatggct | atggtcaaga | gaaagggatc | cggcgccacc | 540 |
| aacttcagcc | tgctgaaaca | ggccggggat | gtggaagaga | accctggccc | ttcgaaaagc | 600 |
| ctgcgggtgc | tgctcgtgat | cctgtggctg | cagctgagct | gggtgtggag | cgcatgccct | 660 |
| gccgtgtacc | agctgagaga | cagcaagagc | agcgacaaga | gcgtgtgcct | gttcaccgac | 720 |
| ttcgacagcc | agaccaacgt | gtcccagagc | aaggactccg | atgtgtacat | caccgataag | 780 |

```
tgcgtgctgg acatgcggag catggacttc aagagcaaca gcgccgtggc ctggtccaac    840
aagagcgatt tcgcctgcgc caacgccttc aacaacagca ttatccccga ggacacattc    900
ttcccaagcc ccgagagcag ctgtgatgtg aagctggtgg aaaagagctt cgagacagac    960
accaacctga acttccagaa cctgagcg                                       988
```

<210> SEQ ID NO 41
<211> LENGTH: 4527
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atggacttcc aggttcagat cttctccttt ctcctgatat ccgcatctgt gattatgtct      60
cggggtcagg tgcagctggt tgaatctgga cctggtgtgg tacagcctgg acggagcctg     120
cgaatctcat gcgctgtctc cggtttctct gtaaccaact atggagtgca ctgggtgcgg     180
cagcctccag gcaagggcct ggaatggctc ggagttatct gggctggcgg aattacaaat     240
tataattccg cttttatgag caggttgaca attagtaaag acaattctaa gaacaccgtt     300
tatcttcaga tgaatagctt gagagctgag gataccgcca tgtactattg tgcatcaaga     360
ggcgggcact acgatacgc gctcgactac tggggacagg gacacttgt gactgtcagt     420 tctggaggcg gtgggagcga ctataaagac gacgatgaca agggtggcgg aggaagcgag     480
atcgtaatga ctcagactcc cgctacactg agtgttagtg ccggagagcg cgttacaatc     540
acttgcaagg catcacaatc tgtttccaac gacgtcactt ggtaccagca gaagcctggg     600
caggctccta gattgctgat ttactccgct agcaatcgct actctggggt ccctgctcgc     660
tttagtggaa gtggctatgg cactgagttt accttcacca tcagcagcgt ccagtcagaa     720
gactttgccg tgtacttctg ccaacaggac tatagctcat tggtcagggg aaccaagctt     780
gagatcaaac gcgtcgacct gaacaaggtg ttcccacccg aggtcgctgt gtttgagcca     840
tcagaagcag agatatccca cacccaaaag gccacactgg tgtgcctggc cacaggcttc     900
ttccccgacc acgtggagct gagctggtgg gtgaatggga aggaggtgca cagtggggtc     960
tgcacggacc cgcagccct caaggagcag cccgccctca tgactccag atactgcctg    1020 agcagccgcc tgagggtctc ggccaccttc tggcagaacc ccgcaacca cttccgctgt    1080 caagtccagt tctacgggct ctcggagaat gacgagtgga cccaggatag ggccaaaccc    1140
gtcacccaga tcgtcagcgc cgaggcctgg ggtagagcag actgtggctt acctcggtg    1200 tcctaccagc aagggtcct gtctgccacc atcctctatg agatcctgct agggaaggcc    1260
accctgtatg ctgtgctggt cagcgccctt gtgttgatgg ctatggtcaa gagaaaggga    1320
tccggcgcca ccaacttcag cctgctgaaa caggccgggg atgtggaaga aaccctggcc    1380
ccttcgaaaa gcctgcgggt gctgctcgtg atcctgtggc tgcagctgag ctgggtgtgg    1440
agcgcatgcc ctgccgtgta ccagctgaga gacagcaaga gcagcgacaa gagcgtgtgc    1500
ctgttcaccg acttcgacag ccagaccaac gtgtcccaga gcaaggactc cgatgtgtac    1560
atcaccgata agtgcgtgct ggacatgcgg agcatggact tcaagagcaa cagcgccgtg    1620
gcctggtcca acaagagcga tttcgcctgc gccaacgcct tcaacaacag cattatcccc    1680
gaggacacat tctcccaag ccccgagagc agctgtgatg tgaagctggt ggaaaagagc    1740
ttcgagacag acaccaacct gaacttccag aacctgagcg tgatcggctt cagaatcctg    1800
```

```
ctgctgaagg tggccggatt caacctgctg atgaccctgc ggctgtggtc ctccgcgggg    1860
agcggcgagg gaagaggatc tctgctaaca tgcggtgacg ttgaggagaa tcccggaccg    1920 cccctcggc tgctgttctt cctgctgttc ctgaccccta tggaagtgcg gcccgaggaa    1980 ccctggtcg tgaaagtgga agagggcgac aacgccgtgc tgcagtgtct gaagggcacc    2040
tccgatggcc ctacccagca gctgacatgg tccagagaga gcccctgaa gcccttcctg    2100 aagctgagcc tgggactgcc tggcctgggc atccatatga ggccactggc catctggctg    2160
ttcatcttca acgtgtccca gcagatgggc ggcttctacc tgtgtcagcc tggcccccca    2220
agcgagaaag cctggcagcc tggctggacc gtgaacgtgg aaggatctgg cgagctgttc    2280
cggtggaacg tgtccgatct gggcggactg ggctgcggcc tgaagaacag aagcagcgag    2340
ggccctagca gccccagcgg caaactgatg agccccaagc tgtacgtgtg gccaaggac    2400 cggcccgaga tttgggaagg cgagcctcct tgcctgcccc ccagagacag cctgaatcag    2460
agcctgagcc aggacctgac aatggcccct ggcagcacac tgtggctgag ctgtggcgtg    2520
ccacccgact ctgtgtccag aggccctctg agctggaccc acgtgcaccc taagggccct    2580
aagagcctgc tgtccctgga actgaaggac gacagacccg ccagagatat gtgggtcatg    2640
gaaaccggcc tgctgctgcc tagagccacc gctcaggatg ccggaaagta ctactgccac    2700
cggggcaacc tgaccatgag cttccacctg gaaatcaccg ccagacccgt gctgtggcac    2760
tggctgctga gaaccggcgg atggaaagtg tccgccgtga ccctggccta cctgatcttc    2820
tgcctgtgct ccctcgtggg catcctgcat ctgcagcggg ctctggtgct gcggcggaag    2880
agaaagagaa tgaccgaccc cacccgcaga ttctaatcac cgtacgtat acacaattgc    2940 atttctctgg cctaactggc cggcacctga ccagatgac ggtggaaaaa ttgcatcata    3000
cagaaggctt ggaggaaaaa ctgtttcaat cactacgctc ggaggaaaat ttgtatcatt    3060
gagatggcct cggcggccag aagccggctg tagagggtat ataatggaag ctcgaattcc    3120
agcctggcct tccggtactg ttggtagaag gcctggcaga gcggcaccgt gggaaaggcc    3180
accatgttgg actttcaagt gcagatcttc agcttcctgc tgatctccgc cagcgtgatc    3240
atgagcagag ccaggtgca gctggtggaa tctggacctg gcgtggtgca gccaggcaga    3300
agcctgagaa tcagctgtgc cgtgtccggc ttcagcgtga ccaactacgg cgtgcactgg    3360
gtgcgccagc ctccaggcaa aggactgaa tggctgggcg tgatctgggc tggcggcatc    3420
accaactaca acagcgcctt catgagccgg ctgaccatca gcaaggacaa cagcaagaac    3480
accgtgtacc tgcagatgaa cagcctgcgg gccgaggaca ccgccatgta ctactgtgct    3540
agcagaggcg ccactacgg ctacgccctg gattattggg gccagggcac actcgtgacc    3600
gtgtctagcg gaggcggagg atctggcggc ggaggaagtg gcggaggggg atctgagatc    3660
gtgatgaccc agacccctgc caccctgtct gtgtctgccg gcgagagagt gaccattacc    3720
tgcaaggcca gccagagcgt gtccaacgac gtgacctggt atcagcagaa gcccggccag    3780
gcccccagac tgctgatcta cagcgccagc aaccggtaca gcggagtgcc cgccagattt    3840
tccggcagcg gctacggcac cgagttcacc ttcaccatca gcagcgtgca gagcgaggac    3900
ttcgccgtgt acttctgtca gcaagactac agcagcttcg gccagggcac caagctggaa    3960
atcaagagat ccggcggagg ctccggctac ccctacgacg tgcccgacta tgcattggac    4020
ctgcggcagg gcatgttcgc ccagctggtg gctcagaacg tgctgctgat cgacggcccc    4080
ctgagctggt actctgatcc tggactggct ggcgtgtccc tgaccggcgg actgagctac    4140
aaagaggaca caaaagaact ggtggtggcc aaggccggcg tgtactacgt gttctttcag    4200
```

```
ctggaactgc ggagagtggt ggccggcgag ggatctggat ctgtgtctct ggccctgcat    4260
ctgcagcccc tgagatctgc tgctggcgca gctgctctgg ctctgaccgt ggatctgcct    4320
cctgccagca gcgaggccag aaacagcgca ttcgggtttc aaggcaggct gctgcacctg    4380
agcgccggac agagactggg agtgcatctg cacacagagg ccagagccag gcacgcctgg    4440
cagctgacac agggcgctac agtgctgggc ctgttcagag tgaccccccga gattcctgcc    4500 ggcctgccta gccctagaag cgaccac                                        4527
```